United States Patent [19]

Dumaitre et al.

[11] Patent Number: 5,663,179
[45] Date of Patent: Sep. 2, 1997

[54] CERTAIN ISOQUINOLINE DERIVATIVES HAVING ANTI-TUMOR PROPERTIES

[75] Inventors: Bernard Andre Dumaitre; Nerina Dodic; Alain Claude-Marie Daugan; Pascal Maurice Charles Pianetti, all of Les Ulis, France

[73] Assignee: Laboratoires Glaxo SA, Paris, France

[21] Appl. No.: 356,323

[22] PCT Filed: Jul. 8, 1993

[86] PCT No.: PCT/EP93/01802

§ 371 Date: Dec. 29, 1994

§ 102(e) Date: Dec. 29, 1994

[87] PCT Pub. No.: WO94/01408

PCT Pub. Date: Jan. 20, 1994

[30] Foreign Application Priority Data

Jul. 10, 1992 [GB] United Kingdom ............... 9214667
Jul. 10, 1992 [GB] United Kingdom ............... 9214668
Jul. 10, 1992 [GB] United Kingdom ............... 9214675

[51] Int. Cl.⁶ ............ C07D 401/12; C07D 407/12; A61K 31/44; A61K 31/47
[52] U.S. Cl. ............ 514/297; 514/309; 514/103; 514/141; 514/142
[58] Field of Search ............ 546/141, 142, 546/103; 514/309, 297

[56] References Cited

FOREIGN PATENT DOCUMENTS

A-0 172 744  2/1986  European Pat. Off. .
A-0 206 802  12/1986  European Pat. Off. .
A-0 494 623  7/1992  European Pat. Off. .

OTHER PUBLICATIONS

Palmer et al., *Journal of Medicinal Chemistry*, vol. 31, No. 3, Mar. 1988, 707–712.
Palmer et al., Journal of Medicinal Chemistry, vol. 31, No. 4, pp. 707–712, Feb. 1988.

*Primary Examiner*—Alan L. Rotman
*Attorney, Agent, or Firm*—Bacon & Thomas

[57] ABSTRACT

Compounds are described of general formula (I)

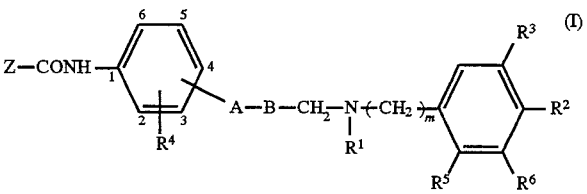

and salts and solvates thereof, including physiologically acceptable salts and solvates thereof, in which:

Z represents either Het,

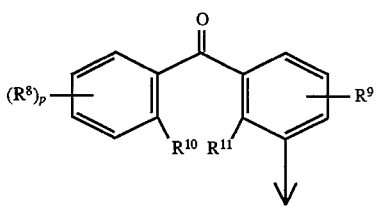

or

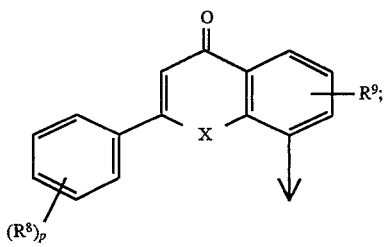

Het represents an optionally substituted bicyclic or tricyclic ring selected from acricine isoquinolin-1-yl, isoquinolin-3-yl, The novel compounds of formula (I) can sensitize multi-drug resistant cancer cells to chemotherapeutic agents and may be formulated for use in therapy, particularly to improve or increase the efficacy of an anti-tumour drug.

11 Claims, No Drawings

CERTAIN ISOQUINOLINE DERIVATIVES HAVING ANTI-TUMOR PROPERTIES

CROSS REFERENCE

This application is a 371 of PCT/EP93/01802 filed 07/08/93

This is invention relates to anilide derivatives, to processes for their preparation, to pharmaceutical compositions containing them, and to their medical use. In particular it relates to compounds and compositions which are capable of sensitizing multidrug-resistant cancer cells to chemotherapeutic agents.

In many patients, the efficacy of cancer chemotherapy is initially poor or decreases after initial treatment due to the development of resistance to anticancer drugs, known as multidrug-resistance. Multidrug-resistance is a process whereby malignant cells become resistant to structurally diverse chemotherapeutic agents following treatment with a single anti-tumour drug. This acquired drug resistance can be a major clinical obstacle in the treatment of cancer. Some tumours are intrinsically multidrug-resistant, and hence do not respond to chemotherapy.

It has been shown that this type of resistance can be reversed by some calcium channel blockers such as nicardipine and verapamil, by antiarrhythmic agents such as amiodarone and quinidine, as well as by natural products such as cepharanthine. However, these compounds exert their multidrug resistant cell sensitizing activity only at very high doses, well above their intrinsic toxic level, and this severely limits their clinical use in the field of cancer chemotherapy.

A novel group of compounds has now been found which can sensitize multidrug-resistant cancer cells to chemotherapeutic agents at dose levels at which these novel compounds show no toxicity.

Thus, the present invention provides a compound of formula (I):

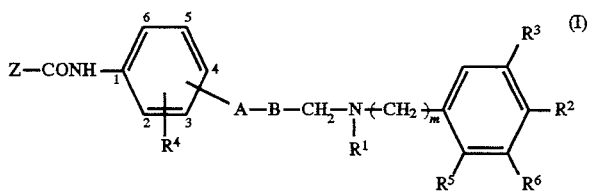

and salts and solvates thereof, including physiologically acceptable salts and solvates thereof, in which:

A represents an oxygen or a sulphur atom, a bond or a group $(CH_2)_lNR^7$ (where l represents zero or 1 and $R^7$ represents a hydrogen atom or a methyl group);

B represents a $C_{1-4}$ alkylene chain optionally substituted by a hydroxyl group, except that the hydroxyl group and moiety A cannot be attached to the same carbon atom when A represents an oxygen or sulphur atom or a group $(CH_2)$ $_lNR^7$, or when A represents a bond B may also represent a $C_{2-4}$ alkenylene chain;

$R^1$ represents a hydrogen atom or a $C_{1-4}$ alkyl group;

m represents 1 or 2;

$R^2$ represents a hydrogen or a halogen atom, or a $C_{1-4}$ alkyl, $C_{1-4}$ alkoxy or $C_{1-4}$ alkylthio group;

$R^3$ represents a hydrogen atom or a $C_{1-4}$ alkoxy group;

$R^4$ represents a hydrogen atom or a $C_{1-4}$ alkyl or $C_{1-4}$ alkoxy group;

$R^5$ represents a hydrogen atom or $R^1$ and $R^5$ together form a group $—(CH_2)_n—$ where n represents 1 or 2;

$R^6$ represents a hydrogen atom or a $C_{1-4}$ alkoxy group; the group

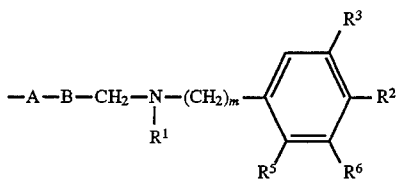

is attached at the benzene ring 3 or 4 position relative to the carboxamide substituent, provided that when the group is attached at the benzene ring 3 position then $R^4$ must be attached at the benzene ring 6 position; and Z represents either Het,

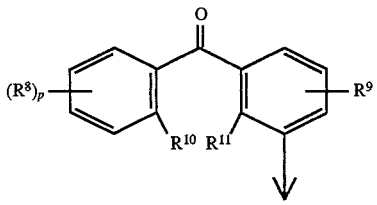

or

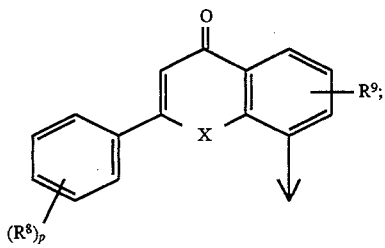

Het represents an optionally substituted bicyclic or tricyclic ring selected from quinolin-4-yl, isoquinolin-1-yl, isoquinolin-3-yl, quinolin-3-yl, quinolin-2-yl, quinoxalin-2-yl, naphthalen-1-yl, naphthalen-2-yl, indol-2-yl, 4-oxo-4H-1-benzopyran-2-yl, phenazin-1-yl and phenothiazin-1-yl or an aryl substituted monocyclic ring selected from 2-aryl-4-thiazolyl, 2-aryl-5-thiazolyl, 5-aryl-2-thienyl, 2-aryl-4-triazolyl and 1-aryl-4-pyrazolyl where aryl represents a phenyl or pyridyl ring optionally substituted by a halogen atom or a trifluoromethyl, $C_{1-4}$ alkyl or $C_{1-4}$ alkoxy group. The above mentioned bicyclic or tricyclic rings may be unsubstituted or substituted by one, two or three groups selected from $C_{1-4}$ alkyl and $C_{1-4}$ alkoxy. Quinolin-4-yl rings may also be substituted in the ring 2 position by phenyl or phenyl substituted by $C_{1-4}$ alkoxy. Indol-2-yl rings may also be substituted in the ring 3 position by benzoyl;

$R^8$ represents a hydrogen or halogen atom or a $C_{1-4}$ alkyl, $C_{1-4}$ alkoxy, $C_{1-4}$ alkylthio, amino or nitro group;

p represents 1; or when $R^8$ represents $C_{1-4}$ alkoxy p may also represent 2 or 3;

$R^9$ represents a hydrogen or halogen atom or a $C_{1-4}$ alkyl, $C_{1-4}$ alkoxy or $C_{1-4}$ alkylthio group;

$R^{10}$ and $R^{11}$ may each represent a hydrogen atom or together form a bond or a linking atom selected from —O— or —S—; and X represents an oxygen atom or $NR^{12}$ (where $R^{12}$ represents a hydrogen atom or a $C_{1-4}$ alkyl group).

As used herein, an alkyl group, either as such or as part of an alkoxy or alkylthio group may be a straight chain or branched chain alkyl group, for example a methyl, ethyl or prop-2-yl group.

A halogen substituent may be a fluorine, chlorine, bromine or iodine atom.

The groups represented by $R^8$ and $R^9$ may be situated at any available positions in the relevant benzene rings.

Examples of the chain —A—B—CH$_2$— include —(CH$_2$)$_2$—, —(CH$_2$)$_3$—, —(CH$_2$)$_4$—, —(CH$_2$)$_5$—, —CH$_2$NMe(CH$_2$)$_2$—, —CH=CHCH$_2$—, —CH$_2$CH=CHCH$_2$—, —CH(OH)CH$_2$—, —O(CH$_2$)$_2$—, —O(CH$_2$)$_3$—, —OCH$_2$CH(OH)CH$_2$—, —NH(CH$_2$)$_2$—, —S(CH$_2$)$_2$— and —S(CH$_2$)$_3$—.

When $R^1$ represents a hydrogen atom or a $C_{1-4}$ alkyl group, preferably $R^1$ represents a $C_{1-4}$ alkyl (e.g. methyl) group.

$R^8$ preferably represents a hydrogen or fluorine atom or a $C_{1-4}$ alkoxy (e.g. methoxy), $C_{1-4}$ alkyl (e.g. methyl) or $C_{1-4}$ alkythio (e.g. methylthio) group.

$R^9$ preferably represents a hydrogen atom or a $C_{1-4}$ alkoxy (e.g. methoxy) group.

A preferred class of compounds of formula (I) is that in which $R^2$ represents a hydrogen atom or a $C_{1-4}$ alkoxy (e.g. methoxy) group, $R^3$ represents a hydrogen atom or a $C_{1-4}$ alkoxy (e.g. methoxy) group and $R^6$ represents a hydrogen atom or a $C_{1-4}$ alkoxy (e.g methoxy) group, provided that at least one of $R^2$, $R^3$ and $R^6$ represents a $C_{1-4}$ alkoxy (e.g. methoxy) group. A particularly preferred class of compounds of formula (I) is that in which $R^2$ and $R^3$ each represent a $C_{1-4}$ alkoxy (e.g. methoxy) group and $R^6$ represents a hydrogen atom.

$R^4$ preferably represents a hydrogen atom or a methyl, ethyl, methoxy or ethoxy group. Compounds of formula (I) in which $R^4$ represents a hydrogen atom are particularly preferred.

A preferred group of compounds of formula (I) is that in which m represents 1 and $R^1$ and $R^5$ together form a group —(CH$_2$)$_2$—, and physiologically acceptable salts and solvates thereof.

A particular group of compounds of formula (I) is that of formula (Ia)

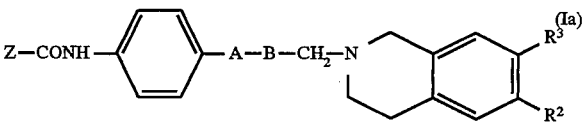

wherein Z is as defined in formula (I) above;
A represents an oxygen or a sulphur atom or a bond;
B represents an unsubstituted $C_{1-4}$ alkylene chain;
$R^2$ and $R^3$ each independently represents a $C_{1-4}$ alkoxy group; (eg methoxy); and physiologically acceptable salts and solvates thereof.

A particular group of compounds of Formula (Ia) are compounds in which Z represents Het as previously defined.

Another particular group of compounds of Formula (Ia) are compounds in which Z represents

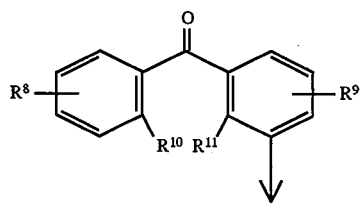

wherein $R^8$ represents a hydrogen or halogen atom or a $C_{1-4}$ alkyl, $C_{1-4}$ alkoxy, $C_{1-4}$ alkylthio or nitro group, $R^9$ represents a hydrogen or halogen atom or a $C_{1-4}$ alkyl, $C_{1-4}$ alkoxy or $C_{1-4}$ alkylthio group and $R^{10}$ and $R^{11}$ are as previously defined.

A further particular group of compounds of formula (Ia) are compounds in which Z represents

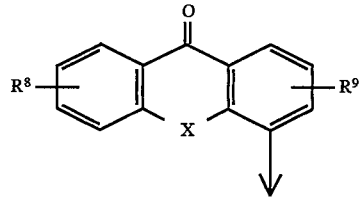

wherein $R^8$ represents a hydrogen or halogen atom or a $C_{1-4}$ alkyl, $C_{1-4}$ alkoxy, $C_{1-4}$ alkylthio or nitro group, $R^9$ represents a hydrogen or halogen atom or a $C_{1-4}$ alkyl, $C_{1-4}$ alkoxy or $C_{1-4}$ alkylthio group and X represents an oxygen atom or NH.

Particularly preferred compounds of formula (Ia) are those in which $R^8$ represents a hydrogen or fluorine atom or a $C_{1-4}$ alkoxy (e.g. methoxy) or $C_{1-4}$ alkyl (e.g. methyl) group and $R^9$ represents a hydrogen atom.

It is to be understood that the present invention includes all combinations of the aforementioned particular and preferred groups.

Suitable physiologically acceptable salts of the compounds of formula (I) include acid addition salts formed with organic or inorganic acids, for example, hydrochlorides, hydrobromides, sulphates, alkyl- or arylsulphonates (e.g. methanesulphonates or p-toluenesulphonates), phosphates, acetates, citrates, succinates, lactates, tartrates, fumarates and maleates. The solvates may, for example, be hydrates.

Other salts which are not physiologically acceptable may be useful in the preparation of compounds of formula (I) and these form a further part of the invention.

The ability of the compounds of formula (I) to sensitize multidrug-resistant cells has been demonstrated in vitro in the multidrug-resistant Chinese hamster ovary cell line (described by Bech-Hansen et al., J. Cell. Physiol., 1976, 88.23–32) and the multidrug-resistant human mammary carcinoma line (described by Batist et al., (J. Biol. Chem., 1986, 261, 1544–1549) using an assay similar to that described by Carmichael et al., Cancer Research, 1987, 47, 936.

The ability of the compounds of formula (I) to sensitize multidrug-resistant cells has also been demonstrated in vivo in the tumour line P388R (described by Johnson et al., Cancer Treat. Rep., 1978, 62, 1535–1547). The methodology used is similar to that described by Boesch et al., Cancer Research, 1991, 51, 4226–4233. However, in our study the compounds were administered orally, intravenously or intraperitoneally in a single dose.

The present invention accordingly provides a compound of formula (I) or a physiologically acceptable salt or solvate thereof for use in therapy, more particularly for use in the treatment of a mammal, including a human, which is suffering from cancer to:

(a) improve or increase the efficacy of an antitumour drug; or (b) increase or restore sensitivity of a tumour to an antitumour drug; or (c) reverse or reduce resistance, whether acquired, induced or inate, of a tumour to an antitumour drug.

The present invention also provides a method of treatment of a mammal, including a human, which is suffering from cancer, which method comprises administering to said mammal an effective amount of a compound of formula (I) or a physiologically acceptable salt or solvate thereof to:

(a) improve or increase the efficacy of an antitumour drug; or (b) increase or restore sensitivity of a tumour to an antitumour drug; or (c) reverse or reduce resistance, whether acquired, induced or inate, of a tumour to an antitumour drug.

In another aspect, the present invention provides the use of a compound of formula (I) or a physiologically acceptable salt or solvate thereof for the manufacture of a medicament for the treatment of a mammal, including a human, which is suffering from cancer to:

(a) improve or increase the efficacy of an antitumour drug; or (b) increase or restore sensitivity of a tumour to an antitumour drug; or (c) reverse or reduce resistance, whether acquired, induced or inate, of a tumour to an antitumour drug.

It will be appreciated that the compounds according to the present invention are administered in conjunction with an antitumour drug. Thus, in a further aspect, the present invention provides a product containing a compound of formula (I) or a physiologically acceptable salt or solvate thereof and an antitumour drug as a combined preparation for simultaneous, separate or sequential use in treating cancer, more particularly to:

(a) improve or increase the efficacy of said antitumour drug; or (b) increase or restore sensitivity of a tumour to an antitumour drug; or (c) reverse or reduce resistance, whether acquired, induced or inate, of a tumour to an antitumour drug.

Examples of suitable antitumour drugs for use in conjunction with compounds of the present invention include Vinca alkaloids (e.g. vincristine, vinblastine and vinorelbine), anthracyclines (e.g. daunorubicin, doxorubicin and aclarubicin), taxol and derivatives thereof (e.g. taxotere), podophyllotoxins (e.g. etoposide and VP16), mitoxantrone, actinomycin, colchicine, gramicidine D, amsacrine or any drug having cross-resistance with the above drugs characterised by the so-called MDR phenotype.

It will be appreciated that if administration of the two drugs is not simultaneous, the delay in administering the second of the active ingredients should not be such as to lose the beneficial effect of the combination.

Thus, in a further aspect, the present invention provides a compound of formula (I) or a physiologically acceptable salt or solvate thereof and an anticancer drug in the presence of each other in the human or non-human animal body for use in treating cancer, more particularly to:

(a) improve or increase the efficacy of said antitumour drug; or (b) increase or restore sensitivity of a tumour to an antitumour drug; or (c) reverse or reduce resistance, whether acquired, induced or inate, of a tumour to an antitumour drug.

Some tumours are often intrinsically multidrug-resistant, notably colon carcinomas, renal cell carcinomas, hepatomas and adrenocortical carcinomas.

Other types of tumour are often initially sensitive but can become multidrug-resistant, notably leukaemias, lymphomas, myelomas, paediatric tumours (e.g. neuroblastomas), sarcomas, and breast, ovarian and lung cancers.

Hence the compounds of the invention are particularly useful in the treatment of mammals, including humans, receiving chemotherapy for one of the above types of cancer.

In using a compound of formula (I) or a physiologically acceptable salt or solvate thereof and an antitumour drug it may be preferable to employ the active ingredients in the form of separate pharmaceutical formulations, although a single combined formulation can be used as demonstrated hereinafter. However, in the latter formulation both active ingredients must of course be stable and mutually compatible in the particular formulation employed.

Pharmaceutical formulations of suitable antitumour drugs and appropriate dosages and dosage rates will generally correspond with those one would use if administering the antitumour drug alone to treat a tumour.

Suitable pharmaceutical formulations and appropriate dosages and dosage rates of compounds of formula (I) and physiologically acceptable salts and solvates thereof are described hereinafter.

Thus, in a further aspect, the invention provides a pharmaceutical composition which comprises a compound of formula (I) or a physiologically acceptable salt or solvate thereof together with one or more physiologically acceptable carriers or excipients.

In another aspect, the present invention provides a pharmaceutical composition which comprises an active amount of a compound of formula (I) or a physiologically acceptable salt or solvate thereof for use in the treatment of a mammal which is suffering from cancer, to:

(a) improve or increase the efficacy of an antitumour drug; or b) increase or restore sensitivity of a tumour to an antitumour drug; or (c) reverse or reduce resistance, whether acquired, induced or inate, of a tumour to an antitumour drug.

The compounds according to the invention may be formulated for oral, buccal, parenteral or rectal administration, of which oral and parenteral are preferred.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. sodium lauryl sulphate or sodium starch glycolate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of the invention may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily, aqueous or alcoholic vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glycerides.

A proposed daily dose of the compounds of the invention for administration to a human (of approximately 70 kg body weight) is about 10 mg to 1000 mg, more preferably about 25 mg to 500 mg. It will be appreciated that it may be necessary to make routine variations to the dosage, depending on the age and condition of the patient, and the route of administration. For example, a daily dose of about 1 mg/kg may be appropriate for administration to a human by infusion. The daily dose may be given as a single unit or as two or more subunits administered after appropriate time intervals.

Compounds of general formula (I) and physiologically acceptable salts and solvates thereof may be prepared by the general methods outlined hereinafter. In the following description, the groups Z, $R^1$ to $R^6$, m, A and B are as defined for compounds of formula (I) unless otherwise specified.

Thus according to a first general process (A), a compound of formula (I) may be prepared by reacting a compound of formula (II):

$$Z-CO_2H \qquad (II)$$

with a compound of formula (III)

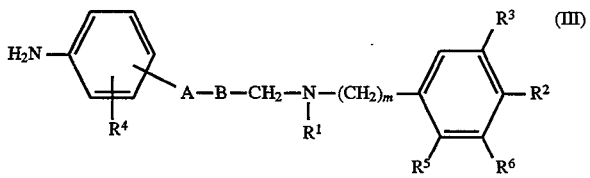

The reaction may be effected using a coupling reagent standardly used in peptide synthesis, such as dicyclohexylcarbodiimide (optionally in the presence of 1-hydroxybenzotriazole), diphenylphosphoryl azide or N,N'-carbonyldiimidazole. The reaction may be conveniently effected in an inert solvent such as an ether (e.g. tetrahydrofuran), a halogenated hydrocarbon (e.g. dichloromethane), an amide (e.g. dimethylformamide) or a ketone (e.g. acetone), and at a temperature of, for example, $-10°$ to $+100°$ C., more preferably at about room temperature.

According to another general process (B), a compound of formula (I) may be prepared by reacting a compound of formula (IV):

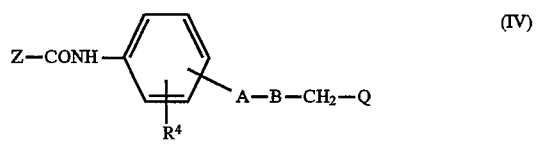

wherein Q represents a halogen (e.g. bromine) atom, with a compound of formula (V):

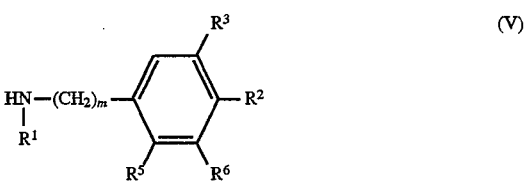

or a salt thereof. The reaction may be effected in the presence of an acid acceptor such as an alkali metal carbonate (e.g. potassium carbonate), in the presence or absence of a solvent, at an elevated temperature (e.g. $50°$ to $120°$ C.). Suitable solvents include ketones (e.g. acetone, methylethylketone or methylisopropylketone) and alcohols (e.g. ethanol or isopropanol).

Compounds of formula (III) may be prepared according to the methodology described in published European Application 0494623.

Compounds of formula (IV) may be prepared by the reaction of a compound of formula (II) as defined previously, with a compound of formula (VI):

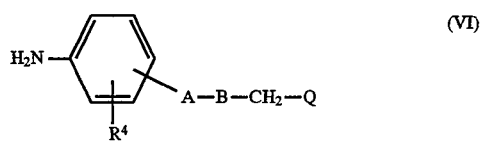

wherein Q represents a halogen (e.g. bromine) atom, under the conditions described in process (A) above for the reaction of a compound of formula (II) with a compound of formula (III).

Intermediates of formula (IV) are novel compounds and represent a further aspect of the present invention.

Compounds of formula (II) are either known in the art or may be prepared by conventional methods, for example as described in the Examples section hereinafter.

Compounds of formulae (V) and (VI) are either known in the art or may be prepared according to the methodology described in published European Application 0494623.

Where it is desired to isolate a compound of the invention as a salt, for example a physiologically acceptable salt, this may be achieved by reacting the compound of formula (I) in the form of the free base with an appropriate acid, preferably with an equivalent amount, in a suitable solvent such as an alcohol (e.g. ethanol or methanol), an aqueous alcohol (e.g. aqueous ethanol), a halogenated hydrocarbon (e.g. dichloromethane), an ester (e.g. ethyl acetate) or an ether (e.g. tetrahydrofuran), or a mixture of two or more of such solvents.

Physiologically acceptable salts may also be prepared from other salts, including other physiologically acceptable salts, of the compound of formula (I) using conventional methods.

The invention is further illustrated by the following Intermediates and Examples which are not intended to limit the invention in any way. All temperatures are in °C. $^1$H NMR spectra were obtained for dilute solutions in $CDCl_3$ unless otherwise stated. Solvents were dried, where indicated, over sodium sulphate. Silica gel used for column chromatography was Merck 60, 230–400 mesh. The following abbreviatons are used: THF—tetrahydrofuran; DMF—dimethylformamide.

INTERMEDIATE 1

Ethyl 3,4-dihydro-6-methoxy-3-oxo-2-quinoxalinecarboxylate 2-amino-4-methoxyaniline (25 g) triethylamine (25.4 ml) and ethanol (250 ml) were stirred under nitrogen at 5°. Diethyl bromomalonate (40.1 ml) in ethanol (50 ml) was added dropwise over 30 min. The mixture was stirred at 5° for 30 minutes. After 16 hours at room temperature, the precipitate was filtered off and stirred in water (800 ml) containing 1N hydrochloric acid (100 ml) for 1 hour. The mixture was filtered. The residue was washed with water and dried in vacuo to give the title compound (15.3 g) as a solid, mp: 227°.

INTERMEDIATE 2

(a) Ethyl 3-chloro-6-methoxy-2-quinoxalinecarboxylate

Phosphorous oxychloride (46 ml) was added to Intermediate 1 (10 g). The mixture was heated at 100° for one hour, allowed to cool, and then carefully poured into ice (800 g). The pH of this mixture was adjusted to 3 by addition of aqueous ammonia. The resulting yellow solid was filtered off, washed with water, and recrystallised from aqueous acetone to give the title compound (10.08 g) as a solid, mp=75°.

The following compound was prepared in a similar manner:

(b) Ethyl 3-chloro-6,7-dimethyl-2-quinolaxinecarboxylate

The title compound (10.7 g) was obtained as a solid, mp=115° from ethyl 3,4-dihydro-3-oxo-6,7-dimethyl-2-quinoxalinecarboxylate* (10 g).
*Chem. Abstracts 41, 3469c.

INTERMEDIATE 3

(a) 3-Methoxy-6,7-dimethyl-2-quinoxalinecarboxylic acid

Intermediate 2(b) (2 g) was added to a solution of sodium (0.43 g) in dry methanol (100 ml). The solution was refluxed for 1 hour, cooled to room temperature and water (20 ml) was added. The solution was refluxed for 1 hour. The cool solution was filtered off. The filtrate was acidified to pH 3 with 2N hydrochloric acid. The product crystallised and was then filtered, washed with water and dried in vacuo to give the title compound (1.59 g) as a solid, mp=180°–182°.

The following compound was prepared in a similar manner:

(b) 3-Ethoxy-6,7-dimethyl-2-quinoxalinecarboxylic acid

The title compound (0.88 g) was obtained as a solid, mp=116°, from Intermediate 2(b) (1.3 g) in ethanol.

INTERMEDIATE 4

Ethyl 6-methoxy-3-ethylthio-2-quinoxalinecarboxylate

To a suspension of sodium hydride (1.8 g) in THF was added a solution of ethanethiol in dry THF (30 ml). After 15 min, a solution of Intermediate 2(a) (10 g) in dry THF (50 ml) was added. The mixture was stirred at room temperature for 16 hours. The precipitate was filtered off and the filtrate was evaporated. The residue was extracted with dichloromethane, washed with water, dried, concentrated in vacuo and recrystallised from isopropanol (50 ml), to give the title compound (5 g) as a solid, mp=70°.

INTERMEDIATE 5

Ethyl 6-methoxy-2-quinoxalinecarboxylate

To a solution of Intermediate 4 (5 g) was carefully added Raney nickel (80 g). The mixture was stirred at room temperature for 1 hour. The Raney nickel was filtered off and the filtrate was concentrated in vacuo. The residue was purified by flash chromatography on silica gel eluting with cyclohexane:ethylacetate (70:30) to give the title compound (2.5 g) as a solid.

NMR includes $\delta 1.48$ (3H,t,CH$_3$); 3.84(3H,s,OCH$_3$); 4.57 (2H,q,CH$_2$).

INTERMEDIATE 6

6-Methoxy-2-quinoxalinecarboxylic acid

To a solution of Intermediate 5 (2.5 g) in ethanol (60 ml) was added an aqueous solution of 30% sodium hydroxide. The mixture was refluxed for 30 minutes. After evaporation, the mixture was acidified by addition of 1N hydrochloric acid. The white crystals were filtered off and dried to give the title compound (2 g) as a solid, mp=248°.

INTERMEDIATE 7

2-Methoxy-3'-methylbenzophenone

A mixture of 2-methoxybenzonitrile (4.3 ml) and the Grignard reagent of m-bromotoluene (6.6 g) in ether was refluxed for 1 h and hydrolysed with dilute hydrochloric acid with heating. The aqueous layer was then extracted with ether, and the resultant organic layer was dried and evaporated to give the title compound (5.5 g) as an oil.

INTERMEDIATE 8

3-(2-Methoxybenzoyl)benzoic acid

A solution of Intermediate 7 (5.4 g) in a mixture of pyridine (50 ml) and water (70 ml) was heated to 50° and treated dropwise with potassium permanganate (19 g). The mixture was then refluxed for 2 h, cooled to room temperature, filtered and the salts were washed with hot water. The aqueous solution was then acidified with sulphuric acid and extracted with dichloromethane. The organic layer was then dried and evaporated to give the title compound (4.4 g) as a solid, mp=170°–172°.

INTERMEDIATE 9

(a) 1-(3-Bromopropoxy)-3-methoxy-4-nitrobenzene

A mixture of 3-methoxy-4-nitrophenol (Intermediate 18 in EP-A-494623) (2.4 g), 1,3-dibromopropane (7.5 ml) and potassium carbonate (2.2 g) in DMF (30 ml) was stirred at room temperature for 24 h. The mixture was filtered and the filtrate was evaporated to dryness. The residue was treated with water and extracted with dichloromethane. The organic extract was then washed with 5% sodium hydroxide solution and brine, dried and concentrated in vacuo to give the title compound (3.5 g) as an oil.

NMR includes $\delta 2.3$ (2H,m,CH$_2$), 3.6 (2H,t,CH$_2$Br), 3.8 (3H,s,OCH$_3$), 4.1 (2H,t, CH$_2$O).

The following compounds were prepared in a similar manner to Intermediate 9(a):

(b) 1-(4-Bromobutoxy)-4-nitrobenzene

The title compound was obtained from 4-nitrophenol and 1,4-dibromobutane.

NMR includes $\delta 4.01$ (2H,m,CH$_2$Br), 3.4 (2H,m,CH$_2$Ar).

(c) 1-(3-Bromopropoxy)-3-methyl-4-nitrobenzene

The title compound (33 g) was obtained as an oil from 3-methyl-4-nitrophenol (25 g) and 1,3-dibromopropane (83 ml).

NMR includes $\delta 2.3$ (2H,m,CH$_2$), 2.5 (3H,s, CH$_3$), 3.6 (2H,t,CH$_2$Br), 4.1 (2H,t, OCH$_2$).

INTERMEDIATE 10

(a) 1,2,3,4-Tetrahydro-6,7-dimethoxy-2-[3-(3-methoxy-4-nitrophenoxy)propyl]isoquinoline A mixture of Intermediate 9(a) (0.7 g), 1,2,3,4-tetrahydro-6,7-dimethoxyisoquinoline (0.4 g) and potassium carbonate (0.36 g) in DMF (25 ml) was heated at 60° for 16 h. The mixture was filtered and the filtrate was evaporated. The residue was treated with water and extracted with dichloromethane. The organic layer was dried, concentrated, and the resultant residue was purified by column chromatography eluting with dichloromethane:methanol (99:1) to give the title compound (0.64 g) as an oil.

NMR includes δ3.8 (9H,2s, 3×OCH$_3$).

The following compounds were prepared in a similar manner to Intermediate 10(a):

(b) 1,2,3,4-Tetrahydro-6,7-dimethoxy-2-[4-(4-nitrophenoxy)butyl]isoquinoline

The title compound was obtained from Intermediate 9(b) and 1,2,3,4-tetrahydro-6,7-dimethoxyisoquinoline.

NMR includes δ3.7(2H,s,NCH$_2$Ar), 3.9(2H,t,OCH$_2$).

(c) 1,2,3,4-Tetrahydro-6,7-dimethoxy-2-[3-(3-methyl-4-nitrophenoxy) propyl]isoquinoline The title compound (5.3 g) was obtained as an oil from Intermediate 9(c) (5.7 g) and 1,2,3,4- tetrahydro-6,7-dimethoxyisoquinoline (4.0 g).

NMR includes δ2.5 (3H,s,CH$_3$), 3.8 (6H,s, 2×OCH$_3$)

(d) N-Methyl-N-(4-nitrobenzyl)veratrylamine

The title compound was obtained as an orange oil from 4-nitrobenzylbromide and N-methylveratrylamine.

NMR includes δ3.8 (6H, s, 2×OCH$_3$), 2.2 (3H, s, NCH$_3$), 3.65 (2H, s, NCH$_2$C$_6$H$_4$NO$_2$-p), 3.5(2H, s, NCH$_2$C$_6$H$_3$(OCH$_3$)$_2$).

(e) N-Methyl-N-[3-(4-nitrophenoxy)propyl]benzylamine

The title compound was obtained as the hydrochloride salt (from diethyl ether) from 1-(3-bromopropoxy)-4-nitrobenzene and N-methylbenzylamine. mp=170°–172°.

INTERMEDIATE 11

(a) 2-Methoxy-4-[3-(1,2,3,4-tetrahydro-6,7-dimethoxy-2-isoquinolinyl)propoxy]benzenamine A solution of Intermediate 10(a) (0.64 g) in ethanol (25 ml) was hydrogenated at room temperature and atmospheric pressure in the presence of 10% palladium on carbon (60 mg). After hydrogen absorption was completed, the catalyst was filtered off and the solution was concentrated in vacuo to give the title compound (0.4 g) as a solid.

NMR includes δ3.8 (9H,s, 3×OCH$_3$), 3.0 (2H,bs,NH$_2$).

The following compounds were prepared in a similar manner to Intermediate 11(a):

(b) 4-[4-(1,2,3,4-Tetrahydro-6,7-dimethoxy-isoquinolinyl)butoxy]benzenamine

The title compound was obtained from Intermediate 10(b), mp=114°.

(c) 2-Methyl-4-[3-(1,2,3,4-tetrahydro-6,7-dimethoxy-2-isoquinolinyl) propoxy]benzenamine The title compound (4.8 g) was obtained as an oil (which subsequently crystallised) from Intermediate 10(c) (5.3 g).

NMR includes δ2.1 (3H,s,CH$_3$), 3.8 (6H,s, 2×OCH$_3$).

(d) N-(4-Aminobenzyl)-N-methylveratrylamine

The title compound was obtained as a yellow oil from Intermediate 10(d).

NMR includes δ3.75 (s, 6H 2×OCH$_3$), 3.5(4H, 2×NCH$_2$Ph), 2.1(3H, s, NCH$_3$).

(e) 4-[3-(N-methylbenzylamino)propoxyaniline

The title compound was obtained as an oil from Intermediate 10(e). NMR includes δ3.9 (t, 2H, O—CH$_2$), 3.4(s, 2H, CH$_2$Ph), 2.1(t, 2H, N—CH$_2$), 2.0(s, 3H, N—CH$_3$), 1.85(m, 2H, CH$_2$).

INTERMEDIATE 12

1-(1,2,3,4-Tetrahydro-6,7-dimethoxy-2-isoquinolinyl) -3- (4-nitrophenoxy)-2-propanol A mixture of 1,2-epoxy-3-(4-nitrophenoxy)propane (4 g) and 6,7-dimethoxy-1,2,3,4-tetrahydroisoquinoline (5.4 g) in isopropanol (100 ml) was heated under reflux for 3 h and evaporated. The residue was purified by column chromatography to give the title compound (7.6 g) as a yellow oil which solidified on standing.

INTERMEDIATE 13

1-(4-Aminophenoxy)-3-(1,2,3,4-tetrahydro-6,7-dimethoxy-2-isoquinolinyl)-2-propanol A solution of Intermediate 12 (4 g) in ethanol (1 00 ml) was hydrogenated at room temperature in the presence of 10% palladium on carbon (0.4 g). After the hydrogen absorption was completed, the catalyst was filtered off and the filtrate concentrated in vacuo to give the title compound (3.5 g) as an off white solid, mp=106°.

INTERMEDIATE 14

3-(3-Methoxybenzoyl)benzoic acid

A solution of 3-methoxy-3'-methylbenzophenone* (8 g) in a mixture of pyridine (50 ml) and water (100 ml) was heated to 50° and treated dropwise with potassium permanganate (22 g). The mixture was then refluxed for 12 h, cooled to room temperature, filtered and the salts washed with hot water. The aqueous solution was then acidified with sulphuric acid and the resultant solid was filtered off and recrystallised from a mixture of ethanol/water to give the title compound (5.8 g) as a solid, mp: 160°.

*W. E. Bachmann and J. W. Ferguson, J. A. C. S., 56, 2081–4 (1934).

INTERMEDIATE 15

3-(4-Fluorobenzoyl)benzoic acid

A suspension of 4'-fluoro-3-methylbenzophenone* (1.8 g) in water (70 ml) was treated dropwise with potassium permanganate (5.3 g) and the mixture was refluxed for 12 h. After cooling to room temperature, the salts were filtered and washed with hot water. The aqueous solution was then acidified with concentrated hydrochloric acid and the resultant solid was filtered off and dried to give the title compound (1.2 g) as a solid, mp: 180°.

*A. Allais et al., Eur. J. Med. Chem.- Chemica therapeutica, 9, n4, p 381–389 (1974).

INTERMEDIATE 16

Methyl 5-(3-fluorobenzoyl)-2-methoxybenzoate

Aluminium trichloride (16.2 g) and 3-fluorobenzoyl chloride (7.5 ml) were added to 1,2-dichloroethane (120 ml) at room temperature. The mixture was cooled to −5° and salicylic acid (8.3 g) was added portionwise and the mixture was heated to 40°. After 12 h at 40°, the mixture was cooled, poured into ice and acidified with 2N hydrochloric acid. Extraction with ethyl acetate and evaporation gave a white solid. A portion (10 g) of the solid was dissolved in dimethylsulphoxide (60 ml) and potassium carbonate (16 g) was added. After 1 h at room temperature, iodomethane (9.6 ml) was added and the mixture was heated at 40° for 3 h. After cooling, the mixture was poured in to ice and the precipitate was purified by chromatogaphy eluting with toluene/ethyl acetate (90/10) to give the title compound (7 g) as a solid, mp: 140°.

INTERMEDIATE 17

N-Benzyl-N-methyl-2-(4-nitrophenoxy)acetamide

MP 95°–96°. Prepared from (4-nitrophenoxy) acetic acid and N-methylbenzylamine according to the method used in Intermediate 34(a) in EP-A-494623.

INTERMEDIATE 18

N-Benzyl-N-methyl-2-(4-aminophenoxy)acetamide as an oil.

NMR includes signals at δ4.8(s, 2H, O—CH$_2$—CO), 3.7(s, 2H, CH$_2$Ph), 2.8(s, 3H, N—CH$_3$). Prepared from Intermediate 17 according to the method used in Intermediate 35(a) in EP-A-494623.

INTERMEDIATE 19

4-[2-(N-Methylbenzylamino)ethoxy]aniline as a red oil. NMR includes signals at δ3.9(t, 2H, O—CH$_2$), 3.5(s, 2H, CH$_2$—Ph), 2.1(t, 2H, N—CH$_2$), 2.0(s,3H, N—CH$_3$). Prepared from Intermediate 18 according to the method used in Intermediate 36(a) in EP-A-494623.

INTERMEDIATE 20

5-(3-Fluorobenzoyl)-2-methoxybenzoic acid

To a suspension of Intermediate 16 (4.3 g) in water (50 ml) was added potassium hydroxide (2.5 g) and the mixture was heated at reflux for 2 h. After cooling, the solution was acidified with 1N hydrochloric acid and the white precipitate was filtered off and dried to give the title compound (4 g) as a solid, mp: 200°.

INTERMEDIATE 21

Methyl 5-benzoyl-2-methoxybenzoate

Aluminium trichloride (16.2 g) and benzoyl chloride (7 ml) were added to 1,2-dichloroethane (100 ml) at room temperature. The mixture was cooled to −5° and salicylic acid (8.3 g) was added portionwise and the mixture was heated to 60°. After 12 h at 60°, the mixture was cooled, poured into ice and acidified with 2N hydrochloric acid. Extraction with ethyl acetate and evaporation gave a white solid which was dissolved in dimethylsulphoxide (100 ml) and potassium carbonate (24 g) was added. After 1 h at room temperature, iodomethane (15 ml) was added and the mixture was heated at 40° for 3 h. After cooling, the mixture was poured in to ice and the precipitate was purified by chromatogaphy on silica gel eluting with toluene/ethyl acetate (90/10) to give the title compound (11.5 g) as a solid, mp: 88°.

INTERMEDIATE 22

5-Benzoyl-2-methoxybenzoic acid

To a suspension of Intermediate 21 (7 g) in water (45 ml) was added potassium hydroxide (4.3 g) and the mixture was heated at reflux for 2 h. After cooling, the solution was acidified with 1N hydrochloric acid and the white precipitate was filtered off and dried to give the title compound (6.1 g) as a solid, mp: 150°.

INTERMEDIATE 23

Methyl 5-(3-methoxybenzoyl)-2-methoxybenzoate

Aluminium trichloride (9.4 g) and 3-methoxybenzoyl chloride (5 ml) were added to 1,2-dichloroethane (60 ml) at room temperature. The mixture was cooled to −5° and salicylic acid (4.8 g) was added portionwise and the mixture was heated to 40°. After 12 h at 40°, the mixture was cooled, poured into ice and acidified with 2N hydrochloric acid. Extraction with ethyl acetate and evaporation gave an oil which was dissolved in dimethylsulphoxide (50 ml) and potassium carbonate (20 g) was added. After 1 h at room temperature, iodomethane (10 ml) was added and the mixture was heated at 40° for 3 h. After cooling, the mixture was poured into ice and the oil was purified by chromatogaphy eluting with toluene/ethyl acetate (90/10) to give the title compound (4.1 g), as a yellow oil.

INTERMEDIATE 24

5-(3-Methoxybenzoyl)-2-methoxybenzoic acid

To a suspension of Intermediate 23 (3.5 g) in water (40 ml) was added potassium hydroxide (1.9 g) and the mixture was heated at reflux for 2 h. After cooling, the solution was acidified with 1N hydrochloric acid and the white precipitate was filtered off and dried to give the title compound (2.5 g) as a solid, mp: 132°.

EXAMPLE 1

N-[4-[3-(1,2,3,4-Tetrahydro-6,7-dimethoxy-2-isoquinolin) propyl]phenyl]-2-quinoxalinecarboxamide A mixture of 2-quinoxalinecarboxylic acid (0.5 g) and 1-hydroxybenzotriazole (0.39 g) in DMF (20 ml) was stirred at room temperature for 10 min. 4-[3-(1,2,3,4-tetrahydro-6, 7-dimethoxy-2-isoquinolinyl)propyl]benzenamine (Intermediate 5(b) in EP-A-494623) (0.78 g) was then added, followed by dicyclohexylcarbodiimide (0.59 g) and the mixture was stirred at room temperature for 16 h and then filtered. The filtrate was concentrated in vacuo, treated with dilute sodium hydroxide solution and extracted with methylene chloride. The combined, dried, organic extracts were evaporated and the residue was purified by column chromatography on silica gel eluting with methylene chloride/methanol (9:1) to give the title compound (0.62 g) as a white solid, after crystallisation from methanol, mp=155°.

Analysis Found: C, 71.41; H, 6.20; N, 11.62; C$_{29}$H$_{30}$N$_4$O$_3$(0.25H$_2$O) Requires: C, 71.51; H, 6.31; N, 11.50%.

The following compounds were prepared in a similar manner:

EXAMPLE 2

N-[4-(3-(Methylveratrylamino)propyl)phenyl]-2-(4-methoxyphenyl)-4-quinolinecarboxamide The coupling of 2-(4-methoxyphenyl)-4-quinolinecarboxylic acid (0.8 g) with 4-amino-N-[(3,4-dimethoxyphenyl)methyl]-N-methylbenzenepropanamine (Intermediate 33(f) in EP-A-494623) (0.9 g) gave, after crystallisation from ethanol, the title compound as a solid (0.75 g), mp=105°.

Analysis Found: C, 75.24; H, 6.49; N, 7.20; C$_{36}$H$_{37}$N$_3$O$_4$ Requires: C, 75.10; H, 6.48; N, 7.30%.

EXAMPLE 3

N-[4-(2-(Methylveratrylamino)ethoxy)phenyl]-2-(3-methoxyphenyl)-4-quinolinecarboxamide The coupling of 2-(3-methoxyphenyl)-4-quinolinecarboxylic acid (0.8 g) with N-[2-(4-aminophenoxy)ethyl]-3,4-dimethoxy-N-methylbenzenemethanamine (Intermediate 36(b) in EP-A-494623) (0.78 g) gave, after crystallisation from diisopropyl ether, the title compound as a solid (0.36 g) mp=97°.

Analysis Found: C, 72.55; H, 6.08; N, 7.23; C$_{35}$H$_{35}$N$_3$O$_5$ Requires: C, 72.77; H, 6.11; N, 7.27%.

EXAMPLE 4

N-[4-[2-[(4-Methoxybenzyl)methylamino]ethoxy]phenyl]-6-methyl-2-phenyl-4-quinolinecarboxamide The coupling of 6-methyl-2-phenyl-4-quinolinecarboxylic acid (1.32 g) with N-[2-(4-aminophenoxy)ethyl]-4-methoxy-N-methylbenzenemethanamine (Intermediate 36(f) in EP-A-494623) (1.2 g) gave the title compound as an oil (0.6 g) in the form of an oxalate (from isopropanol), mp=180°–182°.

Analysis Found : C, 67.66; H, 5.78; N, 6.91; $C_{34}H_{33}N_3O_3$, $C_2H_2O_4$, Hb2O Requires: C, 67.59; H, 5.83; N, 6.57%.

EXAMPLE 5

N-[4-[2-[(4-Methoxybenzyl)methylamino]ethoxy]phenyl]-6-methoxy-2-phenyl-4-quinolinecarboxamide The coupling of 6-methoxy-2-phenyl-4-quinolinecarboxylic acid (0.84 g) with N-[2-(4-aminophenoxy)ethyl]-4-methoxy-N-methylbenzenemethanamine (Intermediate 36(f) in EP-A-494623) (0.87 g) gave after crystallisation from methanol, the title compound as a solid (0.25 g), mp=114°–115°.

Analysis Found: C, 73.94; H, 6.06; N, 7.81; $C_{34}H_{33}N_3O_4$ Requires: C, 74.56; H, 6.07; N, 7.67%.

EXAMPLE 6

N-[4-(4-(Methylveratrylamino)butyl)phenyl]-6-methoxy-2-phenyl-4-quinolinecarboxamide The coupling of 6-methoxy-2-phenyl-4-quinolinecarboxylic acid (1.4 g) with 4-amino-N-[(3,4-dimethoxyphenyl)methyl]-N-methylbenzenebutanamine (Intermediate 33(a) in EP-A-494623) (1.65 g) gave, after crystallisation from ethanol, the title compound as a solid (0.38 g), mp=148°.

Analysis Found: C. 75.26; H, 6.69; N, 6.73; $C_{37}H_{39}N_3O_4$ Requires: C, 75.74; H, 6.18; N, 7.16%.

EXAMPLE 7

N-[4-(2-(Methylveratrylamino)ethyl)phenyl]-1-phenothiazinecarboxamide

The coupling of 1-phenothiazinecarboxylic acid* (0.63 g) with 4-amino-N-[(3,4-dimethoxyphenyl)methyl]-N-methylbenzeneethanamine (Intermediate 33(b) in EP-A-494623) (0.78 g) gave the title compound as an oil (0.4 g) in the form of a hydrochloride (from diethyl ether), mp=144°.

Analysis Found: C, 64.36; H, 5.98; Cl, 5.24; N, 7.15; S, 5.60; $C_{31}H_{31}N_3O_3S_1$, HCl, $H_2O$ Requires: C, 64.18; H, 5.91; Cl, 6.00; N, 7.24; S, 5.53%.
*Brian D Palmer et al., J Med Chem 1988, 31,707–712.

EXAMPLE 8

N-[4-(2-(Methylveratrylamino)ethoxy)phenyl]-1-phenazinecarboxamide

The coupling of 1-phenazinecarboxylic acid* (0.68 g) with N-[2-(4-aminophenoxy)ethyl]-3,4-dimethoxy-N-methylbenzenemethanamine (Intermediate 36(b) in EP-A-494623) (1 g) gave, after crystallisation from ethanol, the title compound as a solid (0.55 g), mp=135°.

Analysis Found: C, 71.30; H, 5.78; N, 10.47; $C_{31}H_{30}N_4O_4$ Requires: C, 71.24; H, 5.78; N, 10.72%.
*Gordon W. Rewcastle et al., J Med Chem. 1987, 30, 843–851.

EXAMPLE 9

N-[4-[2-[(4-Methoxybenzyl)methylamino]ethoxy]phenyl]-1-phenazinecarboxamide

The coupling of 1-phenazinecarboxylic acid (0.68 g) with N-[2-(4-aminophenoxy)ethyl]-4-methoxy-N-methylbenzenemethanamine (Intermediate 36(f) in EP-A-494623) (1 g) gave, after crystallisation from ethanol, the title compound as a solid (0.52 g), mp=134°.

Analysis Found: C, 72.89; H, 5.76; N, 11.54; $C_{30}H_{28}N_4O_3$ Requires: C, 73.15; H, 5.73; N, 11.37%.

EXAMPLE 10

N-[4-(2-(Methylhomoveratrylamino)ethoxy)phenyl]-1-phenothiazine carboxamide

The coupling of 1-phenothiazinecarboxylic acid (0.73 g) with N-[2-(4-aminophenoxy)ethyl]-3,4-dimethoxy-N-methylbenzeneethanamine (Intermediate 36(a) in EP-A-494623) (1.1 g) gave, after crystallisation from ethanol, the title compound as a solid (0.45 g), mp=90°.

Analysis Found: C, 68.98; H, 5.89; N, 7.49; S, 5.59; $C_{32}H_{33}N_3O_4S_1$ Requires: C, 69.16; H, 5.98; N, 7.56; S, 5.77%.

EXAMPLE 11

N-[4-[3-(1,2,3,4-Tetrahydro-6,7-dimethoxy-2-isoquinolinyl)propyl]phenyl]-3-isoquinolinecarboxamide The coupling of 3-isoquinolinecarboxylic acid (0.6 g) with 4-[3-(1,2,3,4-tetrahydro-6,7-dimethoxy-2-isoquinolyl)propyl]benzenamine (Intermediate 5(b) in EP-A-494623) (1 g) gave, after trituration in diethyl ether, the title compound (0.89 g) as a solid, mp=146°.

Analysis Found: C, 73.87; H, 6.15; N, 8.60; $C_{30}H_{31}N_3O_3$ Requires: C, 73.44; H, 6.57; N, 8.56%.

EXAMPLE 12

N-[4-[4-(1,2,3,4-Tetrahydro-6,7-dimethoxy-2-isoquinolinyl)butyl]phenyl]-6,7-dimethyl-2-quinoxalinecarboxamide The coupling of 6,7-dimethyl-2-quinoxalinecarboxylic acid (0.45 g) with 4-[4-(1,2,3,4-tetrahydro-6,7-dimethoxy-2-isoquinolinyl)butyl]benzenamine (Intermediate 2(d) in EP-A-494623) (0.68 g) gave, after crystallisation from isopropanol, the title compound (0.26 g) as a solid, mp=100°–105°.

Analysis Found: C, 70.82; H, 6.89; N, 10.23; $C_{32}H_{36}N_4O_3(H_2O)$ Requires: C, 70.82; H, 7.05; N, 10.32%.

EXAMPLE 13

N-[4-[3-(1,2,3,4-Tetrahydro-6,7-dimethoxy-2-isoquinolinyl)propoxy]phenyl]-6(7)-methyl-2-quinoxalinecarboxamide The coupling of 6(7)-methyl-2-quinoxalinecarboxylic acid* (0.5 g) with 4-[3-(1,2,3,4-tetrahydro-6,7-dimethoxy-2-isoquinolinyl)propoxy]benzenamine (Intermediate 2(a) in EP-A-494623) (0.89 g) gave, after crystallisation from acetonitrile, the title compound (1 g) as a solid, mp=147°.

Analysis Found: C, 70.29; H, 6.33; N, 10.38; $C_{31}H_{34}N_4O_4$ Requires: C, 70.70; H, 6.51; N, 10.64%.
*Chem, Abstracts 53,1358f.

EXAMPLE 14

N-[4-[3-(1,2,3,4-Tetrahydro-6,7-dimethoxy-2-isoquinolinyl)propyl]phenyl]-6(7)-methyl-2-quinoxalinecarboxamide The coupling of 6(7)-methyl-2-quinoxalinecarboxylic acid (0.5 g) with 4-[3-(1,2,3,4-tetrahydro-6,7-dimethoxy-2-isoquinolinyl)propyl]benzenamine (Intermediate 5(b) in EP-A-494623) (0.9 g) gave, after crystallisation from isopropanol, the title compound (1.05 g) as a solid, mp=120°–126°.

Analysis Found: C, 72.88; H, 6.89; N, 10.69; $C_{31}H_{34}N_4O_3$ Requires: C, 72.92; H, 6.71; N, 10.97%.

EXAMPLE 15

N-[4-[4-(1,2,3,4-Tetrahydro-6,7-dimethoxy-2-isoquinolinyl)butyl]phenyl]-6(7)-methoxy-2-quinoxalinecarboxamide The coupling of Intermediate 6 (0.54 g) with 4-[4-(1,2,3,4-tetrahydro-6,7-dimethoxy-2-isoquinolinyl)butyl] benzenamine (Intermediate 2(d) in EP-A-494623) (0.9 g) gave, after crystallisation from a 1:1 mixture of isopropanol and acetonitrile, the title compound (0.93 g) as a solid, mp=138°.

Analysis Found: C, 69.49; H, 6.41; N, 10.30; $C_{31}H_{34}N_4O_4(0.5H_2O)$ Requires: C, 69.51; H, 6.59; N, 10.44%.

EXAMPLE 16

N-[4-[3-(1,2,3,4-Tetrahydro-6,7-dimethoxy-2-isoquinolinyl)propoxy]phenyl]-6(7)-methoxy-2-quinoxalinecarboxamide The coupling of Intermediate 6 (0.54 g) with 4-[3-(1,2,3,4-tetrahydro-6,7-dimethoxy-2-isoquinolinyl)propoxy] benzenamine (Intermediate 2(a) in EP-A-494623) (0.89 g) gave, after crystallisation from a 1:1 mixture of isopropanol and acetonitrile, the title compound (0.9 g) as a solid, mp=166°.

Analysis Found: C, 67.24; H, 5.99; N, 10.48; $C_{30}H_{32}N_4O_5(0.5H_2O)$ Requires: C, 67.02; H, 6.18; N, 10.42%.

EXAMPLE 17

N-[4-[3-(1,2,3,4-Tetrahydro-6,7-dimethoxy-2-isoquinolinyl)propyl]phenyl]-3-quinolinecarboxamide The coupling of 3-quinolinecarboxylic acid (1 g) with 4-[3-(1,2,3,4-tetrahydro-6,7-dimethoxy-2-isoquinolinyl) propyl]benzenamine (Intermediate 5(b) in EP-A-494623) (1.2 g) gave, after crystallisation from isopropanol, the title compound (1.01 g) as a solid, mp=184°–185°.

Analysis Found: C, 74.40; H, 6.50; N, 8.59; $C_{30}H_{31}N_3O_3$ Requires: C, 74.82; H, 6.49; N, 8.73%.

EXAMPLE 18

Hydrochloride salt of N-[4-[4-(1,2,3,4-tetrahydro-6,7-dimethoxy-2-isoquinolinyl)butyl]phenyl]-2-quinolinecarboxamide The coupling of 2-quinolinecarboxylic acid (0.38 g) with 4-[4-(1,2,3,4-tetrahydro-6,7-dimethoxy-2-isoquinolinyl) butyl]benzenamine (Intermediate 2(d) in EP-A-494623) (0.5 g) gave, after crystallisation from isopropanol, the title compound (0.23 g) as a solid, mp=230°–235°.

Analysis Found: C, 69.48; H, 6.45; N, 7.46; $C_{31}H_{34}N_3O_3$ Requires: C, 69.98; H, 6.44; N, 7.90%.

EXAMPLE 19

N-[4-[3-(1,2,3,4-Tetrahydro-6,7-dimethoxy-2-isoquinolinyl)propyl]phenyl]-4-methoxy-2-quinolinecarboxamide The coupling of 4-methoxy-2-quinolinecarboxylic acid (1 g) with 4-[3-(1,2,3,4-tetrahydro-6,7-dimethoxy-2-isoquinolinyl)propyl]benzenamine (Intermediate 5(b) in EP-A-494623) (1 g) gave, after crystallisation from isopropanol, the title compound (0.5 g) as a solid, mp=123°–125°.

Analysis Found: C, 72.70; H, 6.58; N, 8.30; $C_{31}H_{33}N_3O_4$ Requires: C, 72.78; H, 6.50; N, 8.21%.

EXAMPLE 20

N-[4-[4-(Methylveratrylamino)butyl]phenyl]-2-quinoxalinecarboxamide

The coupling of 2-quinoxalinecarboxylic acid (0.5 g) with 4-amino-N-[(3,4-dimethoxyphenyl)methyl]-N-methylbenzenebutanamine (intermediate 33(a) in EP-A-494623) (0.94 g) gave, after crystallisation from ethanol, the title Compound (0.4 g) as a solid, mp=82°–85°.

Analysis Found: C, 71.89; H, 6.73; N, 11.75; $C_{29}H_{32}N_4O_3$ Requires: C, 71.88; H, 6.66; N, 11.56%.

EXAMPLE 21

N-[4-[4-(1,2,3,4-Tetrahydro-6,7-dimethoxy-2-isoquinolinyl)butyl]phenyl]-2-quinoxalinecarboxamide The coupling of 2-quinoxalinecarboxylic acid (0.5 g) with 4-[4-(1,2,3,4-tetrahydro-6,7-dimethoxy-2-isoquinolinyl) butyl]benzenamine (Intermediate 2(d) in EP-A-494623) (0.62 g) gave, after trituration with diethyl ether, the title Compound (0.4 g) as a solid, mp=144°.

Analysis Found: C, 72.33; H, 6.55; $C_{30}H_{32}N_4O_3$ Requires: C, 72.56; H, 6.49%.

EXAMPLE 22

N-[4-[3-(1,2,3,4-Tetrahydro-6,7-dimethoxy-2-isoquinolinyl)propoxy]phenyl]-2-quinoxalinecarboxamide The coupling of 2-quinoxalinecarboxylic acid (0.5 g) with 4-[3-(1,2,3,4-tetrahydro-6,7-dimethoxy-2-isoquinolinyl) propoxy]benzenamine (Intermediate 2(a) in EP-A-494623 (1 g) gave, after recrystallisation from ethanol, the title compound (0.78 g) as a solid, mp=170°–173°.

Analysis Found: C, 69.35; H, 6.16; N, 11.27; $C_{29}H_{30}N_4O_4$ Requires: C, 69.86; H, 6.06; N, 11.24%.

EXAMPLE 23

N-[4-[3-(1,2,3,4-Tetrahydro-6,7-dimethoxy-2-isoquinolinyl)propoxy]phenyl]-3-methoxy-6,7-dimethyl-2-quinoxalinecarboxamide The coupling of Intermediate 3(a) (0.6 g) with 4-[3-(1,2,3,4-tetrahydro-6,7-dimethoxy-2-isoquinolinyl)propoxy] benzenamine (Intermediate 2(a) in EP-A-494623 (0.8 g) gave, after crystallisation from isopropanol, the title compound (0.47 g) as a solid, mp=158°.

Analysis Found: C, 67.32; H, 6.67; N, 9.80; $C_{32}H_{36}N_4O_5$ (0.5H$_2$O) Requires: C, 67.94; H, 6.59; N, 9.90%.

EXAMPLE 24

N-[4-[3-(1,2,3,4-Tetrahydro-6,7-dimethoxy-2-isoquinolinyl)propyl]phenyl]-3-methoxy-6,7-dimethyl-2-quinoxalinecarboxamide The coupling of Intermediate 3(a) (0.6 g) with 4-[3-(1,2,3,4-tetrahydro-6,7-dimethoxy-2-isoquinolinyl)propyl] benzenamine (Intermediate 5(b) in EP-A- 494623) (0.8 g) gave, after crystallisation from isopropanol, the title compound (0.75 g) as a solid, mp=164°–166°.

Analysis Found: C, 67.32; H, 6.67; N, 9.80; $C_{32}H_{36}N_4O_5$ (0.5H$_2$O) Requires: C, 67.94; H, 6.54; N, 9.90%.

EXAMPLE 25

N-[4-[4-(1,2,3,4-Tetrahydro-6,7-dimethoxy-2-isoquinolinyl)butyl]phenyl]-3-methyl-2-quinoxalinecarboxamide

19

The coupling of 3-methyl-2-quinoxalinecarboxylic acid* (0.5 g) with 4-[4-(1,2,3,4-tetrahydro-6,7-dimethoxy-2-isoquinolinyl)butyl]benzenamine (Intermediate 2(d) in EP-A-494623) (0.9 g) gave, after crystallisation from a 1:1 mixture of isopropanol and acetonitrile, the title compound (0.9 g) as a solid, mp=146°.

Analysis Found: C, 73.13; H, 6.76; N, 10.88; $C_{31}H_{34}N_4O_3$ Requires: C, 72.92; H, 6.71; N, 10.97%.

*Chem Abstracts 46,8124c.

EXAMPLE 26

N-[4-[3-(Methylveratrylamino)propyl]phenyl]-5-methoxyindole-2-carboxamide

The coupling of 5-methoxyindole-2-carboxylic acid (0.5 g) with 4-amino-N-[(3,4-dimethoxyphenyl)methyl]-N-methylbenzenepropanamine (Intermediate 33(f) in EP-A-494623) (0.62 g) gave, after crystallisation from isopropanol, the title compound (0.48 g) as a solid, mp=80°.

Analysis Found: C, 70.79; H, 6.86; N, 8.02; $C_{29}H_{33}N_3O_4$ (0.25$H_2O$) Requires: C, 70.78; H, 6.86; N, 8.03%.

EXAMPLE 27

N-[4-[3-(Methylveratrylamino)propyl]phenyl]-3-benzoyl-2-indolecarboxamide

The coupling of 3-benzoyl-2-indolecarboxylic acid (0.35 g) with 4-amino-N-[(3,4-dimethoxyphenyl)methyl]-N-methylbenzenepropanamine (Intermediate 33(f) in EP-A-494623) (0.42 g) gave, after crystallisation from ethanol, the title compound (0.30 g) as a solid, mp=156°–161°.

Analysis Found: C, 74.25; H, 6.36; N, 7.05; $C_{35}H_{35}N_3O_4$ (0.25$H_2O$) Requires: C, 74.24; H, 6.32;,N, 7.42%.

EXAMPLE 28

N-[4-[3-(Methylveratrylamino)propyl]phenyl]-1-naphtalenecarboxamide

The coupling of 1-naphthoic acid (0.3 g) with 4-amino-N-[(3,4-dimethoxyphenyl)methyl]-N-methylbenzenepropanamine (Intermediate 33(f) in EP-A-494623) (0.53 g) gave, after crystallisation from diisopropyl ether, the title compound (0.38 g) as a solid, mp: 113°–117°.

Analysis Found: C, 75.84; H, 6.93; N, 5.92; $C_{30}H_{32}N_2O_3$.0.4$H_2O$ Requires: C, 75.73; H, 6.94; N, 5.88%.

EXAMPLE 29

Oxalate of N-[4-[3-methylveratrylamino]propyl]phenyl]-2-naphtalenecarboxamide

The coupling of 2-naphthoic acid (0.4 g) with 4-amino-N-[(3,4-dimethoxyphenyl)methyl]-N-methylbenzenepropanamine (Intermediate 33(f) in EP-A-494623) (0.73 g) gave the title compound (0.6 g) as a solid, mp: 203°–207°.

Analysis Found: C, 68.76; H, 6.17; N, 5.04; $C_{30}H_{32}N_2O_3.C_2H_2O_4$ Requires: C, 68.80; H, 6.13; N, 5.01%.

EXAMPLE 30

N-[4-[4-(1,2,3,4-Tetrahydro-6,7-dimethoxy-2-isoquinolinyl)butyl]phenyl]-2-naphtalenecarboxamide The coupling of 2-naphthoic acid (0.6 g) with 4-[4-(1,2,3,4-tetrahydro-6,7-dimethoxy-2-isoquinolinyl)butyl]benzenamine (Intermediate 2(d) in EP-A-494623) (0.79 g) gave, after crystallisation from isopropanol, the title compound (0.5 g) as a solid, mp: 165°–167°.

Analysis Found : C, 76.84; H, 6.92; N, 5.59; $C_{32}H_{34}N_2O_3$.0.3$H_2O$ Requires: C, 76.86; H, 6.97; N, 5.60%.

EXAMPLE 31

N-[4-[2-(1,2,3,4-Tetrahydro-6,7-dimethoxy-2-2isoquinolinyl)ethyl]phenyl]-2-naphtalenecarboxamide The coupling of 2-naphthoic acid (0.47 g) with 4-[2-(1,2,3,4-tetrahydro-6,7-dimethoxy-2-isoquinolinyl)ethyl] benzenamine (Intermediate 2(c) in EP-A-494623) (0.82 g) gave, after crystallisation from isopropanol, the title compound (0.83 g) as a solid, mp: 162°–165°.

Analysis Found : C, 77.28; H, 6.50; N, 5.91; $C_{30}H_{30}N_2O_3$ Requires: C, 77.23; H, 6.48; N, 6.00%.

EXAMPLE 32

N-[4-[3-(1,2,3,4-Tetrahydro-6,7-dimethoxy-2-isoquinolinyl)propoxy]phenyl]-2-naphtalenecarboxamide The coupling of 2-naphthoic acid (0.3 g) with 4-[3-(1,2,3,4-tetrahydro-6,7-dimethoxy-2-isoquinolinyl)propoxy] benzenamine (Intermediate 2(a) in EP-A-494623) (0.58 g) gave, after crystallisation from acetonitrile, the title compound (0.2 g) as a solid, mp: 189°–190°.

Analysis Found: C, 74.97; H, 6.53; N, 5.54; $C_{31}H_{32}N_2O_4$ Requires: C, 74.98; H, 6.50; N, 5.64%.

EXAMPLE 33

N-[4-[3-(Methylveratrylamino)propoxy]phenyl]-2-naphtalenecarboxamide

The coupling of 2-naphthoic acid (0.4 g) with N-[3-(4-aminophenoxy)propyl]-3,4-dimethoxy-N-methylbenzenemethanamine (Intermediate 38(c) in EP-A-494623) (0.76 g) gave, after crystallisation from acetonitrile, the title compound (0.45 g) as a solid, mp: 131°–133°.

Analysis Found: C, 74.22; H, 6.75; N, 5.78; $C_{30}H_{32}N_2O_4$ Requires: C, 74.36; H, 6.66; N, 5.78%.

EXAMPLE 34

Oxalate of N-[4-[3-methylveratrylamino]propyl]phenyl]-1-isoquinolinecarboxamide

The coupling of 1-isoquinolinecarboxylic acid (0.35 g) with 4-amino-N-[(3,4-dimethoxyphenyl)methyl]-N-methylbenzenepropanamine (Intermediate 33(c) in EP-A-494623) (0.53 g) gave the title compound (0.3 g) as a solid, mp: 183°–187°.

Analysis Found: C, 66.65; H, 6.00; N, 7.40; $C_{29}H_{31}N_3O_3.C_2H_2O_4$ Requires: C, 66.53; H, 5.94; N, 7.51%.

EXAMPLE 35

N-[4-[3-(1,2,3,4-Tetrahydro-6,7-dimethoxy-2-isoquinolinyl)propoxy]phenyl]-1-isoquinolinecarboxamide The coupling of 1-isoquinolinecarboxylic acid (0.35 g) with 4-[3-(1,2,3,4-tetrahydro-6,7-dimethoxy-2-isoquinolinyl)propoxy]benzenamine (Intermediate 2(a) in EP-A-494623) (0.58 g) gave, after crystallisation from isopropanol, the title compound (0.6 g) as a solid, mp: 160°.

Analysis Found: C, 72.61; H, 6.39; N, 8.43; $C_{30}H_{31}N_3O_4$ Requires: C, 72.41; H, 6.28; N, 8.44%.

EXAMPLE 36

Oxalate of N-[4-[3-(1,2,3,4-tetrahydro-6,7-dimethoxy-2-isoquinolinyl)propyl]phenyl]-1-isoquinolinecarboxamide The coupling of 1-isoquinolinecarboxylic acid (0.35 g) with 4-[3-(1,2,3,4-tetrahydro-6,7-dimethoxy-2-isoquinolinyl)propyl]benzenamine (Intermediate 5(b) in EP-A-494623) (0.55 g) gave the title compound (0.5 g) as a solid, mp: 206°–209°.

Analysis Found: C, 66.56; H, 5.87; N, 7.30; $C_{30}H_{31}N_3O_3C_2H_2O_4 0.3H_2O$ Requires: C, 66.60; H, 5.87; N, 7.28%.

EXAMPLE 37

N-[4-[4-(1,2,3,4-Tetrahydro-6,7-dimethoxy-2-isoquinolinyl)butyl]phenyl]-3(2-methoxybenzoyl) benzamide The coupling of Intermediate 8 (0.56 g) with 4-[4-(1,2,3,4-tetrahydro-6,7-dimethoxy-2-isoquinolinyl)butyl]benzenamine (Intermediate 2(d) in EP-A-494623) (0.67 g) gave the title compound (0.31 g) as an amorphous solid, mp=78°.

Analysis Found: C, 71.35; H, 6.68; N, 4.82; $C_{36}H_{38}N_2O_5 1.5H_2O$ Requires: C, 71.38; H, 6.82; N, 4.62%

EXAMPLE 38

Fumarate of N-[4-[3-methylveratrylamino]propyl]phenyl]-2-indolecarboxamide

The coupling of 2-indolecarboxylic acid (0.3 g) with 4-amino-N-[(3,4-dimethoxyphenyl)methyl]-N-methylbenzenepropanamine (Intermediate 33(f) in EP-A-494623) (0.58 g) gave the title compound (0.3 g) as a solid, mp=196°.

Analysis Found: C, 69.79; H, 6.36; N, 8.21; $C_{28}H_{31}N_3O_3C_4H_4O_4$ Requires: C, 69.88; H, 6.45; N, 8.15%.

EXAMPLE 39

N-[4-[4-(1,2,3,4-Tetrahydro-6,7-dimethoxy-2-isoquinolinyl)butoxy]phenyl]-6(7)-methyl-2-quinoxalinecarboxamide The coupling of 6(7)-methyl-2-quinoxalinecarboxylic acid (0.5 g) with Intermediate 11(b) (0.94 g) gave, after crystallisation from a 1:1 mixture of isopropanol and acetonitrile, the title compound (1.09 g) as a solid, mp=142°–148°.

Analysis Found: C, 70.86; H, 6.49; N, 10.40; $C_{31}H_{34}N_4O_4$ Requires: C, 70.70; H, 6.51; N, 10.64%.

EXAMPLE 40

N-[4-[4-(1,2,3,4-Tetrahydro-6,7-dimethoxy-2-isoquinolinyl)butoxy]phenyl]-1-isoquinolinecarboxamide The coupling of 1-isoquinolinecarboxylic acid (0.5 g) with Intermediate 11(b) (0.89 g) gave, after crystallisation from methanol, the title compound (0.6 g) as a solid, mp=122°–123°.

Analysis Found: C, 72.73; H, 6.62; N, 8.12; $C_{31}H_{33}N_3O_4$ Requires: C, 72.78; H, 6.50; N, 8.21%.

EXAMPLE 41

N-[4-[4-(1,2,3,4-Tetrahydro-6,7-dimethoxy-2-isoquinolinyl)butoxy]phenyl]-2-quinoxalinecarboxamide The coupling of 2-quinoxalinecarboxylic acid (0.5 g) with Intermediate 11(b) (0.89 g) gave, after crystallisation from acetonitrile, the title compound (0.97 g) as a solid, mp=141°.

Analysis Found: C, 69.62; H, 6.29; N, 10.93; $C_{30}H_{32}N_4O_4(0.3H_2O)$ Requires: C, 69.55; H, 6.34; N, 10.81%.

EXAMPLE 42

N-[4-[4-(1,2,3,4-Tetrahydro-6,7-dimethoxy-2-isoquinolinyl)butoxy]phenyl]-3-ethoxy-2-quinoxalinecarboxamide The coupling of 3-ethoxy-2-quinoxalinecarboxylic acid (0.5 g) with Intermediate 11(b) (0.63 g) gave, after crystallisation from ethanol, the title compound (0.48 g) as a solid, mp=182°.

Analysis Found: C, 72.08; H, 4.51; N, 16.86; $C_{18}H_{11}N_3O$ Requires: C, 72.28; H, 4.45; N, 16.86%.

EXAMPLE 43

N-[4-[4-(1,2,3,4-Tetrahydro-6,7-dimethoxy-2-isoquinolinyl:)butoxy]phenyl]-4-[2-(4-chlorophenyl)-3-trifluoromethylpyrazole]carboxamide The coupling of 2-(4-chlorophenyl)-3-trifluoromethylpyrazole-4-carboxlic acid (1 g) with Intermediate 11(b) (1.3 g) gave the title compound (1.8 g), mp=153°.

Analysis Found: C, 60.87; H, 5.11; N, 8.77; $C_{32}H_{32}ClF_3N_4O_4$ Requires: C, 61.10; H, 5.13; N, 8.91%.

EXAMPLE 44

N-[4-[4-(1,2,3,4-Tetrahydro-6,7-dimethoxy-2-isoquinolinyl)butoxy]phenyl]-5-[4-methyl-2-[4-trifluoromethyl)phenyl]thiazole]carboxamide The coupling of 4-methyl-2-[4-(trifluoromethyl)phenyl]thiazole-5-carboxylic acid (1 g) with Intermediate 11(b) (1 g) gave, after crystallisation from methanol/ethanol (1:1), the title compound (0.7 g), mp=160°–180°.

Analysis Found: C, 62.95; H, 5.33; F, 9.06;, N,6.52; $C_{33}H_{34}F_3N_3O_4S$ Requires: C, 63.35; H, 5.48; F, 9.11; N, 6.72%.

EXAMPLE 45

N-[4-[3-(1,2,3,4-Tetrahydro-6,7-dimethoxy-2-isoquinolinyl)propoxy]phenyl]-2-[5-(2-pyridyl)lthiophene] carboxamide The coupling of 5-(2-pyridyl)thiophene-2-carboxylic acid (1 g) with 4-[3-(1,2,3,4-tetrahydro-6,7-dimethoxy-2-isoquinolinyl)propoxy]benzenamine (Intermediate 2(a) in EP-A-494623) (1.3 g) gave, after crystallisation from methanol, the title compound (1.5 g), mp=196°.

Analysis Found: C, 67.96; H, 5.88; N, 7.86; $C_{30}H_{31}N_3O_4S$ Requires: C, 68.03; H, 5.90; N, 7.93%.

EXAMPLE 46

N-[4-[3-(1,2,3,4-Tetrahydro-6,7-dimethoxy-2-isoquinolinyl)propoxy]phenyl]-4-[2-(3-pyridyl)thiazole] carboxamide The coupling of 2-(3-pyridyl)thiazole-4-carboxylic acid (1 g) with 4-[3-(1,2,3,4-tetrahydro-6,7-dimethoxy-2-isoquinolinyl)propoxy]benzenamine (Intermediate 2(a) in EP-A-494623) gave, after crystallisation from isopropanol/methanol, the title compound (1.2 g), mp=125°.

Analysis Found: C, 65.30; H, 5.11; N, 10.32; $C_{29}H_{30}N_4O_4S$ Requires: C, 65.64; H, 5.70; N, 10.56%

EXAMPLE 47

N-[4-[3-(1,2,3,4-Tetrahydro-6,7-dimethoxy-2-isoquinolinyl)propoxy]phenyl]-5-(4-methyl-2-phenyl-1,2,3-triazole) carboxamide The coupling of 4-methyl-2-phenyl-1,2,3-triazole-5-carboxylic acid (1 g) with 4-[3-(1,2,3,4-tetrahydro-6,7-dimethoxy-2-isoquinolinyl)propoxy]benzenamine (Intermediate 2(a) in EP-A-494623) (1.6 g) gave, after crystallisation from methanol/pyridine (5:1) the title compound (1.6 g), mp=146°.

Analysis Found: C, 67.28; H, 6.10; N, 13.20; $C_{30}H_{33}N_5O_4(0.5H_2O)$ Requires: C, 67.14; H, 6.38; N, 13.05%.

EXAMPLE 48

N-[4-[3-(1,2,3,4-Tetrahydro-6,7-dimethoxy-2-isoquinolinyl)-2-hydroxypropoxy]phenyl]-2-quinoxalinecarboxamide The coupling of 2-quinoxalinecarboxylic acid (0.5 g) with Intermediate 13 (1 g) gave the title compound (0.9 g) as a solid, mp=158°–160°.

Analysis Found: C, 65.68; H, 5.99; N, 10.23; $C_{29}H_{30}N_4O_5(1H_2O)$ Requires: C, 65.40; H, 6.05; N,10.52%.

EXAMPLE 49

N-[4-(2-(Methylveratrylamino)ethyl)phenyl]-2-(4-methoxyphenyl)-4-quinolinecarboxamide The coupling of 2-(4-methoxyphenyl)-4-quinolinecarboxylic acid (0.8 g) with 4-amino-N-[(3,4-dimethoxyphenyl)methyl]-N-methylbenzeneethanamine (Intermediate 33(b) in EP-A-494623) (0.86 g) gave, after crystallisation from ethanol, the title compound as a solid (0.33 g), mp=114°.

Analysis Found: C, 74.72; H, 6.29; N, 7.29; $C_{35}H_{35}N_3O_4$ Requires: C, 74.84; H, 6.28; N, 7.48%.

EXAMPLE 50

N-[4-(3-(Methylveratrylamino)propyl)phenyl]-2-(3-methoxyphenyl)-4-quinolinecarboxamide The coupling of 2-(3-methoxyphenyl)-4-quinolinecarboxylic acid (0.8 g) with 4-amino-N-[(3,4-dimethoxyphenyl)methyl]-N-methylbenzenepropanamine (Intermediate 33(f) in EP-A-494623) (0.9 g) gave, after crystallisation from isopropanol, the title compound as a solid (0.51 g), mp=110°.

Analysis Found: C, 75.10; H, 6.52; N, 7.26; $C_{36}H_{37}N_3O_4$ Requires: C, 75.10; H, 6.48; N, 7.30%.

EXAMPLE 51

N-[4-[2-(Methylveratrylamino)ethyl]phenyl)-9-oxo-4-thioxanthenecarboxamide

A mixture of 9-oxo-4-thioxanthenecarboxylic acid* (0.8 g) and 1-hydroxybenzotriazole (0.42 g) in DMF (20 ml) was stirred at room temperature for 10 min. 4-Amino-N-[(3,4-dimethoxyphenyl)methyl]-N-methylbenzenemethanamine (Intermediate 33(b) in EP-A-494623) (0.94 g) in DMF (20 ml) was then added, followed by dicyclohexylcarbodiimide (0.64 g) and the mixture was stirred at room temperature for 16 h and then filtered. The filtrate was concentrated in vacuo, treated with dilute sodium hydroxide solution and extracted with dichloromethane. The combined dried organic extracts were evaporated to leave an oil which was purified by column chromatography eluting with dichloromethane: methanol (95:5). The resulting solid was recrystallised from acetonitrile and filtered off to give the title compound as a solid (0.26 g),mp=180°.

Analysis Found: C, 71.02; H, 5.59; N, 5.18; S, 5.78; $C_{32}H_{30}N_2O_4S_1$ Requires: C, 71.35; H, 5.61; N, 5.20; S, 5.95%.

Chem.Abstracts 99,5518d.

The following examples were prepared in a similar manner:

EXAMPLE 52

N-[4-(3-(Methylveratrylamino)propyl)phenyl]-5-methoxy-9-oxo-4-thioxanthenecarboxamide The coupling of 5-methoxy-9-oxo-4-thioxanthenecarboxylic acid* (0.8 g) with 4-amino-N-[(3,4-dimethoxyphenyl)methyl]-N-methylbenzenepropanamine (Intermediate 33(f) in EP-A-494623) (0.88 g) gave, after crystallisation from acetonitrile, the title compound as a solid (0.12 g), mp=144°–146°.

Analysis Found: C, 69.49; H, 5.86; N, 4.75; S, 5.33; $C_{34}H_{34}N_2O_5S_1$ Requires: C, 70.08; H, 5.88; N, 4.81; S, 5.50%.

*prepared from 2-(methoxyphenylthio)isophtalic acid** in sulphuric acid, mp>200°, IR includes peaks at 1660 cm$^{-1}$(CO) and 1700cm$^{-1}$($CO_2H$), by a method analogous to that described in Chem. Abstracts 99, 5518d.

**prepared from 2-iodorsophtalic acid and 2-methoxythiophenol, mp=208°, IR includes a broad band at 1700–1720 cm$^{-1}$ ($CO_2H$), by a method analogous to that described in Chem. Abstracts 99, 5518d.

EXAMPLE 53

N-[4-(2-(Methylveratrylamino)ethyl)phenyl]-5-methoxy-9-oxo-4-thioxanthenecarboxamide The coupling of 5-methoxy-9-oxo-4-thioxanthenecarboxylic acid (0.8 g) with 4-amino-N-[(3,4-dimethoxyphenyl)methyl]-N-methylbenzeneethanamine (Intermediate 33(b) in EP-A-494623) (0.8 g) gave, after crystallisation from acetonitrile, the title compound as a solid (0.1 g) mp=151°.

Analysis Found: C. 67.98; H, 5.66; N, 4.79; S, 5.29; $C_{33}H_{32}N_2O_5S_1.H_2O$ Requires: C, 67.55; H, 5.84; N, 4.77; S, 5.46%.

EXAMPLE 54

N-[4-(3-(Methylveratrylamino)propoxy)phenyl]-9-oxo-4-thioxanthenecarboxamide

The coupling of 9-oxo-4-thioxanthenecarboxylic acid (0.8 g) with 4-amino-N-[[(3,4-dimethoxyphenyl)methyl]-N-methylbenzeneethanamine (Intermediate 33(b) in EP-A-494623) (1 g) gave, after crystallisation from ethanol, the title compound as a solid (0.47 g), mp=184°.

Analysis Found: C, 69.67; H, 5.68; N, 4.93; S, 5.52; $C_{33}H_{32}N_2O_5S_1$ Requires: C, 69.69; H, 5.67; N, 4.93; S, 5.64%.

EXAMPLE 55

N-[4-(2-(Methylveratrylamino)ethyl)phenyl]-7-fluoro-9-oxo-4-thioxanthenecarboxamide The coupling of 7-fluoro-9-oxo-4-thioxanthenecarboxylic acid* (0.8 g) with 4-amino-N-[(3,4-dimethoxyphenyl) methyl]-N-methylbenzeneethanamine (Intermediate 33(b) in EP-A-494623) (0.87 g) gave, after crystallisation from ethanol, the title compound as a solid (0.3 g), mp=205°.

Analysis Found: C, 68.99; H, 5.23; F, 3.31; N, 4.99; S, 5.58; $C_{32}H_{29}F_1N_2O_4S_1$ Requires: C, 69.04; H, 5.25; F, 3.41; N, 5.03; S, 5.76%.

*prepared from 2-(4-fluorophenylthio)isophtalic acid** in sulphuric acid, mp>200°, IR includes peaks at 1660cm$^{-1}$ (CO) and 1700cm$^{-1}$($CO_2H$), by a method analogous to that described in Chem. Abstracts 99, 5518d.

**prepared from 2-iodoisophtalic acid and 4-fluorothiophenol, mp=204°–205°, IR includes a large band at 1700 cm$^{-1}$ ($CO_2H$).

EXAMPLE 56

N-[4-(3-(Methylveratrylamino)propyl)phenyl]-7-fluoro-9-oxo-4-thioxanthenecarboxamide The coupling of 7-fluoro-9-oxo-4-thioxanthenecarboxylic acid (0.8 g) with 4-amino-N-[(3,4-dimethoxyphenyl)methyl]-N-methylbenzenepropanamine (Intermediate 33(f) in EP-A-494623) (0.9 g) gave, after crystallisation from acetonitrile, the title compound as a solid (0.3 g) mp=160°.

Analysis Found: C, 69.24; H, 5.46; F, 3.20; N, 4.85; S, 5.49; $C_{33}H_{31}F_1N_2O_4S_1$ Requires: C, 69.45; H, 5.48; F, 3.33; N, 4.91; S, 5.62%.

EXAMPLE 57

N-[4-(4-(1Methylveratrylamino)butyl)phenyl]-7-fluoro-9-oxo-4-thioxanthenecarboxamide The coupling of 7-fluoro-9-oxo-4-thioxanthenecarboxylic acid (0.4 g) with 4-amino-N-[(3,4-dimethoxyphenyl)methyl]-N-methylbenzenebutanamine (Intermediate 33(a) in EP-A-494623) (0.48 g) gave, after crystallisation from ethanol the title compound as a solid (0.076 g), mp=168°.

Analysis Found: C, 69.80; H, 5.77; F, 3.24; N, 4.66; S, 5.42; $C_{34}H_{33}F_1N_2O_4S_1$ Requires: C, 69.84; H, 5.69; F, 3.25; N, 4.79; S, 5.48%.

EXAMPLE 58

N-[4-(3-(Methylveratrylamino)propylthio)phenyl]-9-oxo-4-thioxanthenecarboxamide

The coupling of 9-oxo-4-thioxanthenecarboxylic acid (0.8 g) with N-[3-[(4-aminophenyl)thio]propyl]-3,4-dimethoxy-N-methylbenzenemethanamine (Intermediate 38(d) in EP-A-494623) (1 g) gave, after crystallisation from ethanol, the title compound as a solid (0.1 g), mp=148°.

Analysis Found: C, 67.73; H, 5.35; N, 4.71; S, 10.85; $C_{33}H_{32}N_2O_4S_2$ Requires: C, 67.78; H, 5.52; N, 4.79; S, 10.96%.

EXAMPLE 59

N-[4-(Methylveratrylamino)methyl)phenyl]-9-oxo-4-thioxanthenecarboxamide

The coupling of 9-oxo-4-thioxanthenecarboxylic acid (0.8 g) with Intermediate 11(d) (0.9 g) gave, after crystallisation from ethanol, the title compound as a solid (0.1 g), mp=166°.

Analysis Found: C, 70.85; H, 5.38; N, 5.50; S, 5.90; $C_{31}H_{28}N_2O_4S_1$ Requires: C, 70.97; H, 5.38; N, 5.34; S, 6.11%.

EXAMPLE 60

N-[4-[3-(1,2,3,4-Tetrahydro-6,7-dimethoxy-2-isoquinolinyl)propoxy]phenyl]-9-oxo-4-thioxanthenecarboxamide The coupling of 9-oxo-4-thioxanthenecarboxylic acid (0.8 g) with 4-[3-(1,2,3,4-tetrahydro-6,7-dimethoxy-2-isoquinolinyl)propoxy]benzenamine (Intermediate 2(a) in EP-A-494623) (1.14 g) gave, after crystallisation from acetonitrile, the title compound as a solid (0.35 g), mp=210°.

Analysis Found: C, 70.29; H, 5.51; N, 4.89; S, 5.52; $C_{34}H_{32}N_2O_5S_1$ Requires: C, 70.32; H, 5.55; N, 4.83; S, 5.52%.

EXAMPLE 61

N-[4-[2-(1,2,3,4-Tetrahydro-6,7-dimethoxy-2-isoquinolinyl)ethyl]phenyl]-5-methoxy-9-oxo-4-thioxanthenecarboxamide The coupling of 5-methoxy-9-oxo-4-thioxanthenecarboxylic acid (3 g) with 4-[2-(1,2,3,4-tetrahydro-6,7-dimethoxy-2-isoquinolinyl)ethyl]benzenamine (Intermediate 2(c) in EP-A-494623) (3 g) gave, after crystallisation from methanol, the title compound as a solid (1.38 g), mp=218°–219°.

NMR includes signals at δ2.8(4H,m,N-$(CH_2)_2$-Ph); 3.7 (6H,s,2$OCH_3$); 3.8(3H,s,$OCH_3$).

EXAMPLE 62

N-[4-(2-Methylhomoveratrylamino)ethoxy)phenyl]-9-oxo-4-xanthenecarboxamide

The coupling of 9-oxo-4-xanthenecarboxylic acid (0.33 g) with N-[2-(4-aminophenoxy)ethyl]-3,4-dimethoxy-N-methylbenzeneethanamine (Intermediate 36(a) in EP-A-494623) (0.45 g) gave, after crystallisation from ethanol, the title compound as a solid (0.15 g), mp=152°.

Analysis Found: C, 71.54; H, 5.85; N, 5.07; $C_{33}H_{32}N_2O_6$ Requires: C, 71.72; H, 5.84; N, 5.07%.

EXAMPLE 63

N-[4-(2-(Methylhomoveratrylamino)ethoxy)phenyl]-9-oxo-4-thioxanthenecarboxamide

The coupling of 9-oxo-4-thioxanthenecarboxylic acid (0.8 g) with N-[2-(4-aminophenoxy)ethyl]-3,4-dimethoxy-N-methylbenzeneethanamine (Intermediate 36(a) in EP-A-494623) (1 g) gave, after crystallisation from acetonitrile, the title compound as a solid (0.35 g), mp=168°.

Analysis Found: C, 69.71; H, 5.67; N, 4.91; S, 5.50; $C_{33}H_{32}N_2O_5S_1$ Requires: C, 69.69; H, 5.67; N, 4.93; S, 5.64%.

EXAMPLE 64

N-[4-(2-(Methylveratrylamino)ethoxy)phenyl]-9-oxo-4-thioxanthenecarboxamide

The coupling of 9-oxo-4-thioxanthenecarboxylic acid (1 g) with N-[2-(4-aminophenoxy)ethyl]-3,4-dimethoxy-N-methylbenzenemethanamine (Intermediate 36(b) in EP-A-494623) (1.23 g) gave, after crystallisation from acetonitrile, the title compound as a solid (0.2 g), mp=188°.

Analysis Found: C, 68.89; H, 5.75; N, 5.50; S, 5.46; $C_{32}H_{30}N_2O_5S_1$ Requires: C. 69.29; H, 5.46; N, 5.05; S, 5.78%.

EXAMPLE 65

N-[4-(3-(Methylhomoveratrylamino)propoxy)phenyl]-9-oxo-4-thioxanthenecarboxamide The coupling of 9-oxo-4-thioxanthenecarboxylic acid (0.8 g) with N-[3-(4-aminophenoxy)propyl]-3,4-dimethoxy-N-methylbenzeneethanamine (Intermediate 38(a) in EP-A-494623) (1 g) gave, after crystallisation from acetonitrile, the title compound as a solid (0.6 g), mp=174°.

Analysis Found: C, 69.70; H, 5.89; N, 4.70; S, 5.39; $C_{34}H_{34}N_2O_5S_1$ Requires: C, 70.08; H, 5.88; N, 4.81; S, 5.50%.

EXAMPLE 66

N-[4-(4-(Methylveratrylamino)butyl)phenyl]-9-oxo-4-thioxanthenecarboxamide

The coupling of 9-oxo-4-thioxanthenecarboxylic acid (0.77 g) with 4-amino-N-[(3,4-dimethoxyphenyl)methyl]-N-methylbenzenebutanamine (Intermediate 33(a) in EP-A-494623) (0.98 g) gave, after crystallisation from ethanol, the title compound as a solid (0.27 g), mp=156°.

Analysis Found: C, 71.82; H, 6.00; N, 5.06; S, 5.63; $C_{34}H_{34}N_2O_4S_1$ Requires: C, 72.05; H, 6.05; N, 4.94; S, 5.66%.

EXAMPLE 67

N-[4-(4-(Methylhomoveratrylamino)butyl)phenyl]-7-fluoro-9-oxo-4-thioxanthenecarboxamide The coupling of 7-fluoro-9-oxo-4-thioxanthenecarboxylic acid (1 g) with 4-amino-N-[2-(3,4-dimethoxyphenyl)ethyl]-N-methylbenzenebutanamine (Intermediate 33(c) in EP-A-494623) (1.25 g) gave, after crystallisation from ethanol, the title Compound as a solid (0.95 g), mp=145°.

Analysis Found: C, 69.87; H, 5.79; F, 2.95; N, 4.30; S, 5.35; $C_{35}H_{35}F_1N_2O_4S_1$ Requires: C, 70.21; H, 5.89; F, 3.17; N, 4.68; S, 5.35%.

EXAMPLE 68

N-[4-(2-(Methylhomoveratrylamino)ethoxy)phenyl]-7-fluoro-9-oxo-4-thioxanthenecarboxamide The coupling of 7-fluoro-9-oxo-4-thioxanthenecarboxylic acid (1 g) with N-[2-(4-aminophenoxy)ethyl]-3,4-dimethoxy-N-methylbenzeneethanamine (Intermediate 36(a) in EP-A-494623) (1.2 g) gave, after crystallisation from ethanol, the title compound as a solid (0.72 g), mp=145°.

Analysis Found: C, 67.42; H, 5.26; F, 2.92; N, 4.92; S, 5.85; $C_{33}H_{31}F_1N_2O_5S_1$ Requires: C, 67.56; H, 5.33; F, 3.24; N, 4.77; S, 5.46%.

EXAMPLE 69

N-[4-(2-(Methyveratrylamino)ethoxy)phenyl]-9-oxo-4-xanthenecarboxamide

The coupling of 9-oxo-4-xanthenecarboxylic acid (0.6 g) with N-[2-(4-aminophenoxy)ethyl]-3,4-dimethoxy-N-methylbenzenemethanamine (Intermediate 36(b) in EP-A-494623) (0.79 g) gave, after crystallisation from ethanol, the title compound as a solid (0.21 g), mp=110°.

Analysis Found: C, 71.17; H, 5.59; N, 5.29; $C_{32}H_{30}N_2O_6$ Requires: C, 71.36; H, 5.62; N, 5.20%.

EXAMPLE 70

N-[4-(2-(Methylhomoveratrylamino)ethyl)phenyl]-9-oxo-4-thioxanthenecarboxamide

The coupling of 9-oxo-4-thioxanthenecarboxylic acid (0.8 g) with 4-amino-N-[2-(3,4-dimethoxyphenyl)ethyl]-N-methylbenzeneethanamine (Intermediate 33(e) in EP-A-494623) (1 g) gave, after crystallisation from acetonitrile, the title compound as a solid (0.43 g), mp=154°.

Analysis Found: C, 71.83; H, 5.92; N, 5.08; S, 5.89; $C_{33}H_{32}N_2O_4S_1$ Requires: C, 71.71; H, 5.84; N, 5.07; S, 5.80%.

EXAMPLE 71

N-[4-(4-(Methylhomoveratrylamino)butyl)phenyl]-9-oxo-4-xanthenecarboxamide

The coupling of 9-oxo-4-xanthenecarboxylic acid (0.3 g) with 4-amino-N-[2-(3,4-dimethoxyphenyl)ethyl]-N-methylbenzenebutanamine (Intermediate 33(c) in EP-A-494623) (0.42 g) gave, after crystallisation from ethanol, the title compound as a solid (0.09 g), mp=102°.

Analysis Found: C, 73.58; H, 6.36; N, 5.07; $C_{35}H_{36}N_2O_5$ Requires: C, 74.44; H, 6.43; N, 4.96%.

EXAMPLE 72

N-[4-(3-(Methylhomoveratrylamino)propoxy)phenyl]-9-oxo-4-xanthenecarboxamide

The coupling of 9-oxo-4-xanthenecarboxylic acid (0.6 g) with N-[3-(4-aminophenoxy)propyl]-3,4-dimethoxy-N-methylbenzeneethanamine Intermediate 38(a) in EP-A-494623) (1.04 g) gave, after crystallisation from ethanol, the title compound as a solid (0.26 g), mp=126°.

Analysis Found: C, 71.27; H, 6.06; N, 4.84; $C_{34}H_{34}N_2O_6$ Requires: C, 72.07; H, 6.05; N, 4.94%.

EXAMPLE 73

N-[4-[4-[(4-Methylthiobenzyl)methylamino]butyl]phenyl]-9-oxo-4-thioxanthenecarboxamide The coupling of 9-oxo-4-thioxanthenecarboxylic acid (0.8 g) with 4-amino-N-[[4-(methylthio)phenyl]methyl]-N-methylbenzenebutanamine (Intermediate 33(j) in EP-A-494623) (1 g) gave, after crystallisation from acetonitrile, the title compound as a solid (0.39 g), mp=167°.

Analysis Found: C, 71.47; H, 5.78; N, 5.13; S, 11.50; $C_{33}H_{32}N_2O_2S_2$ Requires: C, 71.70; H, 5.84; N, 5.07; S, 11.60%.

EXAMPLE 74

N-[4-[3-[(4-Methoxybenzyl)methylamino]propyl]phenyl]-9-oxo-4-thioxanthenecarboxamide The coupling of 9-oxo-4-thioxanthenecarboxylic acid (0.77 g) with 4-amino-N-[(4-methoxyphenyl)methyl]-N-methylbenzenepropanamine (Intermediate 33(g) in EP-A-494623) (0.85 g) gave, after crystallisation from ethanol, the title compound as a solid (0.34 g), mp=170°.

Analysis Found: C, 73.22; H, 5.84; N, 5.35; S, 5.89; $C_{32}H_{30}N_2O_3S_1$ Requires: C, 73.53; H, 5.78; N, 5.36; S, 6.13%.

EXAMPLE 75

N-[4-(3-(Methylhomoveratrylamino)propyl)phenyl]-9-oxo-4-thioxanthenecarboxamide

The coupling of 9-oxo-4-thioxanthenecarboxylic acid (0.6 g) with 4-amino-N-[2-(3,4-dimethoxyphenyl)ethyl]-N-methylbenzenepropanamine (Intermediate 33(d) in EP-A-494623) (1 g) gave, after crystallisation from acetonitrile, the title compound as a solid (0.35 g), mp=143°.

Analysis Found: C, 72.10; H, 5.91; N, 4.70; S, 5.48; $C_{34}H_{34}N_2O_4S_1$ Requires: C, 72.06; H, 6.05; N, 4.94; S, 5.66%.

EXAMPLE 76

N-N-[2-[(4-Methoxyphenethyl)methylamino]ethyl]phenyl]-9-oxo-4-thioxanthenecarboxamide The coupling of 9-oxo-4-thioxanthenecarboxylic acid (0.4 g) with 4-amino-N-[2-(4-methoxyphenyl)ethyl]-N-methylbenzeneethanamine (Intermediate 33(k) in EP-A-494823) (0.44 g) gave, after crystallisation from ethanol, the title compound as a solid (0.13 g), mp=163°.

Analysis Found: C, 72.49; H, 5.80; N, 5.35; S, 5.97; $C_{32}H_{30}N_2O_3S_1$ Requires: C, 73.53; H, 5.79; N, 5.36; S, 6.13%.

EXAMPLE 77

N-[4-(5-(Methylveratrylamino)pentyl)phenyl]-9-oxo-4-thioxanthenecarboxamide

The coupling of 9-oxo-4-thioxanthenecarboxylic acid (0.4 g) with 4-amino-N-[(3,4-dimethoxyphenyl)methyl]-N-methylbenzenepentanamine (Intermediate 33(l) in EP-A-494623) (0.53 g) gave, after crystallisation from ethanol, the title compound as a solid (0.2 g), mp=166°.

Analysis Found: C, 72.31; H, 6.22; N, 4.85; S, 5.39; $C_{35}H_{36}N_2O_4S_1$ Requires: C, 72.38; H, 6.25; N, 4.82; S, 5.52%.

EXAMPLE 78

N-[4-(3-(Methylveratrylamino)propyl)phenyl]-9-oxo-4-thioxanthenecarboxamide

The coupling of 9-oxo-4-thioxanthenecarboxylic acid (3 g) with 4-amino-N-[(3,4-dimethoxyphenyl)methyl]-N-methylbenzenepropanamine (Intermediate 33(f) in EP-A-494623) (3.7 g) gave, after crystallisation from ethanol, the title compound as a solid (2.5 g), mp=150°.

Analysis Found: C, 71.70; H, 5.88; N, 5.06; S, 5.72; $C_{33}H_{32}N_2O_4S_1$ Requires: C, 71.71; H, 5.84; N, 5.07; S, 5.80%.

EXAMPLE 79

N-[4-[3-(Methylveratrylamino)propyl]phenyl]-9-fluorenone-4-carboxamide

The coupling of 9-fluorenone-4-carboxylic acid (0.5 g) with 4-amino-N-[(3,4-dimethoxyphenyl)methyl]-N-methylbenzenepropanamine (Intermediate 33(f) in EP-A-494623) (0.63 g) gave, after crystallisation from ethanol, the title compound (0.75 g) as a solid, mp=50°–75°.

Analysis Found: C, 75.12; H, 6.38; N, 5.23; $C_{33}H_{32}N_2O_4$ (0.4H$_2$O) Requires: C, 75.09; H, 6.26; N, 5.23%.

EXAMPLE 80

Fumarate of N-[4-[3-(1,2,3,4-tetrahydro-6,7-dimethoxy-2-isoquinolinyl)propylthio]phenyl]-3-benzoylbenzamide The coupling of 3-benzoylbenzoic acid (0.5 g) with 4-[[3-(1,2,3,4-tetrahydro-6,7-dimethoxy-2-isoquinolinyl)propyl]thio]benzenamine (Intermediate 2(b) in EP-A-494623) (0.79 g) gave the title compound (0.4 g) as a solid, mp: 192°.

Analysis Found: C, 66.94; H, 5.68; N, 4.07; $C_{34}H_{34}N_2O_4S.C_4H_4O$ Requires: C, 66.85; H, 5.61; N, 4.10%.

EXAMPLE 81

Oxalate of N-[4-[3-(methylveratrylamino)propoxy]phenyl]-3-benzoylbenzamide

The coupling of 3-benzoylbenzoic acid (0.8 g) with N-[3-(4-aminophenoxy)propyl]-3,4-dimethoxy-N-methylbenzenemethanamine (Intermediate 38(c) in EP-A-494623) (1.17 g) gave the title compound (1.2 g) as a solid, mp: 168°.

Analysis Found: C, 66.92; H, 5.79; N, 4.42; $C_{33}H_{34}N_2O_5.C_2H_2O_4$ Requires: C, 66.87; H, 5.77; N, 4.46%.

EXAMPLE 82

Fumarate of N-[4-[4-(methylveratrylamino)]butyl]phenyl]-3-benzoylbenzamide

The coupling of 3-benzoylbenzoic acid (0.8 g) with 4-amino-N-[(3,4-dimethoxyphenyl)methyl]-N-methylbenzenebutanamine (Intermediate 33(a) in EP-A-494623) (1.16 g) gave the title compound (1.2 g) as a solid, mp: 182°.

Analysis Found: C, 70.06; H, 6.19; N, 4.22; $C_{34}H_{36}N_2O_4.C_4H_4O_4$ Requires: C, 69.92; H, 6.18; N, 4.29%.

EXAMPLE 83

N-[4-[2-(Methylveratrylamino)ethyl]phenyl]-3-benzoylbenzamide

The coupling of 3-benzoylbenzoic acid (0.22 g) with 4-amino-N-[(3,4-dimethoxyphenyl)methyl]-N-methylbenzeneethanamine (Intermediate 33(b) in EP-A-494623) (0.3 g) gave, after crystallisation from diisopropyl ether, the title compound (0.28 g) as a solid, mp: 130°.

Analysis Found: C, 75.19; H, 6.37; N, 5.50; $C_{32}H_{32}N_2O_4$ Requires: C, 75.57; H, 6.34; N, 5.51%.

EXAMPLE 84

Fumarate of N-[4-[4-(1,2,3,4-tetrahydro-6,7-dimethoxy-2-isoquinolinyl)butyl]phenyl]-3-benzoylbenzamide The coupling of 3-benzoylbenzoic acid (0.8 g) with 4-[4-(1,2,3,4-tetrahydro-6,7-dimethoxy-2-isoquinolinyl)butyl]benzenamine (Intermediate 2(d) in EP-A-494623) (1.2 g) gave the title compound (0.3 g) as a solid, mp: 198°.

Analysis Found: C, 70.36; H, 6.03; N, 4.08; $C_{35}H_{36}N_2O_4.C_4H_4O_4$ Requires: C, 70.46; H, 6.06; N, 4.21%.

EXAMPLE 85

N-[4-[3-(1,2,3,4-Tetrahydro-6,7-dimethoxy-2-isoquinolinyl)propoxy]phenyl]-3-benzoylbenzamide The coupling of 3-benzoylbenzoic acid (1 g) with 4-[3-(1,2,3,4-tetrahydro-6,7-dimethoxy-2-isoquinolinyl)propoxy]benzenamine (Intermediate 2(a) in EP-A-494623) (1.5 g) gave, after crystallisation from isopropanol, the title compound (1.3 g) as a solid, mp:>260°.

Analysis Found: C, 74.12; H, 6.18; N, 5.16; $C_{34}H_{34}N_2O_5$ Requires: C, 74.15; H, 6.22; N, 5.08%.

EXAMPLE 86

Oxalate of N-[2-methoxy-4-[3-(1,2,3,4-tetrahydro-6,7-dimethoxy-2-isoquinolinyl)propoxy]phenyl]-3-benzoylbenzamide The coupling of 3-benzoylbenzoic acid (0.6 g) with Intermediate 11(a) (0.98 g) gave the title compound (1 g) as a solid, mp: 158°.

Analysis Found: C, 66.29; H, 5.72; N, 4.10; $C_{35}H_{36}N_2O_6.C_2H_2O_4$ Requires: C, 66.26; H, 5.71; N, 4.18%.

EXAMPLE 87

Fumarate of N-[4-[2-(1,2,3,4-tetrahydro-6,7-dimethoxy-2-isoquinolinyl)ethyl]phenyl]-3-benzoylbenzamide The coupling of 3-benzoylbenzoic acid (0.6 g) with 4-[2-(1,2,3,4-tetrahydro-6,7-dimethoxy-2-isoquinolinyl)ethyl]benzenamine (Intermediate 2(c) in EP-A-494623) (0.82 g) gave the title compound (1 g) as a solid, mp: 134°.

Analysis Found: C, 70.87; H, 5.84; N, 4.33; $C_{33}H_{32}N_2O_4.½C_4H_4O_4.1.5H_2O$ Requires: C, 70.98; H, 6.04; N, 4.73%.

EXAMPLE 88

Oxalate of N-[2-methyl-4-[2-(1,2,3,4-tetrahydro-6,7-dimethoxy-2-isoquinolinyl)ethyl]phenyl]-3-benzoylbenzamide The coupling of 3-benzoylbenzoic acid (0.86 g) with 2-methyl-4-[2-(1,2,3,4-tetrahydro-6,7-dimethoxy-2-isoquinolinyl)ethyl]benzenamine (Intermediate 16(c) in EP-A-494623) (1.25 g) gave the title compound (0.6 g) as a solid, mp: 230°.

Analysis Found: C, 72.19; H, 6.06; N, 4.54; $C_{34}H_{34}N_2O_4.½C_2H_2O_4$ Requires: C, 72.51; H, 6.08; N, 4.83%.

EXAMPLE 89

Fumarate of N-[4-[4-(1,2,3,4-tetrahydro-6,7-dimethoxy-2-isoquinolinyl)butyl]phenyl]-3-(3-methoxybenzoyl)benzamide The coupling of Intermediate 14 (0.5 g) with 4-[4-(1,2,3,4-tetrahydro-6,7-dimethoxy-2-isoquinolinyl)butyl]benzenamine (Intermediate 2(d) in EP-A-494623) (0.63 g) gave, the title compound (0.7 g) as a solid, mp: 188°.

Analysis Found: C, 69.13; H, 6.04; N, 4.13; $C_{36}H_{38}N_2O_5.C_4H_4O_4$ Requires: C, 69.15; H, 6.09; N, 4.03%.

EXAMPLE 90

Fumarate of N-[4-[4-(1,2,3,4-tetrahydro-6,7-dimethoxy-2-isoquinolinyl)butyl]phenyl]-3-(4-fluorobenzoyl)benzamide The coupling of Intermediate 15 (0.46 g) with 4-[4-(1,2,3,4-tetrahydro-6,7-dimethoxy-2-isoquinolinyl)butyl]benzenamine (Intermediate 2(d) in EP-A-494623) (0.64 g) gave, the title compound (0.25 g) as a solid, mp: 176°.

Analysis Found: C, 68.51; H, 5.85; F, 2.86; N, 4.31; $C_{35}H_{35}FN_2O_4.C_4H_4O_4$ Requires: C, 68.61; H, 5.76; F, 2.78; N, 4.10%.

EXAMPLE 91

Fumarate of N-[4-[4-(1,2,3,4-tetrahydro-6,7-dimethoxy-2-isoquinolinyl)butyl]phenyl]-3-(4-methoxybenzoyl)benzamide The coupling of 3-(4-methoxybenzoyl)benzoic acid* (0.4 g) with 4-[4-(1,2,3,4-tetrahydro-6,7-dimethoxy-2-isoquinolinyl)butyl]benzenamine (Intermediate 2(d) in EP-A-494623) (0.53 g) gave the title compound (0.55 g) as a solid, mp: 178°.

Analysis Found: C, 68.85; H, 6.01; N, 4.12; $C_{36}H_{38}N_2O_5.C_4H_4O_4$ Requires: C, 69.15; H, 6.09; N, 4.03%.

*A. I. Meyers et al., J. Amer. Chem. Soc., 91 (21), 5886–87 (1969).

EXAMPLE 92

Oxalate of N-[4-[4-(1,2,3,4-tetrahydro-6,7-dimethoxy-2-isoquinolinyl)butyl]phenyl]-5-(3-fluorobenzoyl)-2-methoxy-benzamide The coupling of Intermediate 20 (0.5 g) with 4-[4-(1,2,3,4-tetrahydro-6,7-dimethoxy-2-isoquinolinyl)butyl]benzenamine (Intermediate 2(d) in EP-A-494623) (0.62 g) gave, the title compound (0.6 g) as a solid, mp: 112°.

Analysis Found: C, 66.23; H, 5.73; F, 2.85; N, 4.02; $C_{36}H_{37}FN_2O_5.C_2H_2O_4$ Requires: C, 66.46; H, 5.72; F, 2.77; N, 4.08%.

EXAMPLE 93

Oxalate of N-[4-[4-(1,2,3,4-tetrahydro-6,7-dimethoxy-2-isoquinolinyl)butyl]phenyl]-5-benzoyl-2-methoxybenzamide The coupling of Intermediate 22 (0.5 g) with 4-[4-(1,2,3,4-tetrahydro-6,7-dimethoxy-2-isoquinolinyl)butyl]benzenamine (Intermediate 2(d) in EP-A-494623) (0.66 g) gave the title compound (1 g) as a solid, mp: 202°.

Analysis Found: C, 68.16; H, 6.04; N, 4.13; $C_{36}H_{38}N_2O_5.C_2H_2O_4$ Requires: C, 68.25; H, 6.03; N, 4.19%.

EXAMPLE 94

Oxalate of N-[4-[4-(1,2,3,4-tetrahydro-6,7-dimethoxy-2-isoquinolinyl)butyl]phenyl]5-(3-methoxybenzoyl)-2-methoxybenzamide The coupling of Intermediate 24 (0.5 g) with 4-[4-(1,2,3,4-tetrahydro-6,7-dimethoxy-2-isoquinolinyl)butyl]benzenamine (Intermediate 2(d) in EP-A-494623) (0.59 g) gave the title compound (0.8 g) as a solid, mp: 116°.

Analysis Found: C, 65.24; H, 6.18; N, 3.81; $C_{37}H_{40}N_2O_6.C_2H_2O_4.1H_2O$ Requires: C, 65.35; H, 6.18; N, 3.90%.

EXAMPLE 95

Oxalate of N-[4-[4-(1,2,3,4-tetrahydro-6,7-dimethoxy-2-isoquinolinyl)butyl]phenyl]-5-(3-methylbenzoyl)-2-methoxybenzamide The coupling of 5-(3-methylbenzoyl)-2-methoxybenzoic acid* (0.42 g) with 4-[4-(1,2,3,4-tetrahydro-6,7-dimethoxy-2-isoquinolinyl)butyl]benzenamine (Intermediate 2(d) in EP-A-494623) (0.53 g) gave the title compound (0.45 g) as a solid, mp: 114°.

Analysis Found: C, 67.56; H, 6.34; N, 3.89; $C_{37}H_{40}N_2O_5.C_2H_2O_4.\frac{1}{2}H_2O$ Requires: C, 67.71; H, 6.26; N, 4.04%.

*Fuji Yasao et al., Nippon Noyaku Gakkaishi, 4 (4), 511–514 (1979).

EXAMPLE 96

Fumarate of N-[2-methyl-4-[3-(1,2,3,4-tetrahydro-6,7-dimethoxy-2-isoquinolinyl)propoxy]phenyl]-3-benzoylbenzamide The coupling of 3-benzoylbenzoic acid (1 g) with Intermediate 11(c) (1.4 g) gave the title compound (0.9 g) as a solid, mp=94°.

Analysis Found: C, 65.30; H, 6.16; N, 4.13; $C_{35}H_{36}N_2O_5C_4H_4O_4.2H_2O$ Requires: C, 65.35; H, 6.18; N, 3.90%.

EXAMPLE 97

N-[4-(4-((4-Fluorobenzyl)methylamino)butyl)phenyl]-9-oxo-4-thioxanthenecarboxamide The coupling of 9-oxo-4-thioxanthenecarboxylic acid (0.72 g) with 4-amino-N-[(4-fluorophenyl)methyl]-N-methylbenzenebutanamine (Intermediate 33(i) in EP-A-494623) (0.86 g) gave, after crystallisation from ethanol, the title compound as a solid (0.37 g), mp=168°.

Analysis Found: C, 72.54; H, 5.57; F, 3.62; N, 5.92; S, 5.76; $C_{32}H_{29}F_1N_2O_2S_1$ Requires: C, 73.26; H, 5.57; F, 3.62; N, 5.34; S, 6.11%.

EXAMPLE 98

N-[2-Methyl-4-[3-(1,2,3,4-tetrahydro-6,7-dimethoxy-2-isoquinolinyl)propoxy]phenyl]-3-benzoylbenzamide The coupling of 3-benzoylbenzoic acid (1 g) with Intermediate 11(c) (1.46 g) gave the title compound as an oil (0.86 g), fumarate (from isopropanol), mp=94°.

Analysis Found: C, 65.30; H, 6.16; N, 4.13; $C_{35}H_{36}N_2O_5, C_4H_4O_4, 2H_2O$ Requires: C, 65.34; H, 6.18; N, 3.90%.

EXAMPLE 99

Fumarate of N-[4-[3-(1,2,3,4-tetrahydro-6,7-dimethoxy-2-isoquinolinyl)-2-hydroxypropoxy]phenyl]-3-benzoylbenzamide The coupling of 3-benzoylbenzoic acid (0.5 g) with Intermediate 13 (0.79 g) gave the title compound (0.7 g) as a solid, mp=160°.

Analysis Found: C, 66.92; H, 5.57; N, 4.05; $C_{34}H_{34}N_2O_6C_4H_4O_4$ Requires: C, 66.85; H, 5.61; N, 4.10%.

EXAMPLE 100

Fumarate of N-[4-[3-(1,2,3,4-tetrahydro-6,7-dimethoxy-2-isoquinolinyl)-2-hydroxypropoxy]phenyl]-3-(4-fluorobenzoyl)benzamide The coupling of Intermediate 15 (0.36 g) with Intermediate 13 (0.44 g) gave the title compound (0.2 g) as a solid, mp=162°–164°.

Analysis Found: C, 65.15; H, 5.41; F, 2.65; N, 4.05; $C_{34}H_{33}FN_2O_6C_4H_4O_4$ Requires: C, 65.14; H, 5.32; F, 2.71; N, 4.00%.

EXAMPLE 101

Oxalate of N-[4-[3-(methylbenzylamino)propoxy]phenyl]-3-benzoylbenzamide

The coupling of 3-benzoylbenzoic acid (0.7 g) with Intermediate 11(e) (0.83 g) gave the title compound (1.1 g) as a solid, mp=172°.

Analysis Found: C, 69.92; H, 5.69; N, 4.94; $C_{31}H_{30}N_2O_3C_2H_2O_4$ Requires: C, 69.71; H, 5.67; N, 4.93%.

EXAMPLE 102

Oxalate of N-[4-[3-(1,2,3,4-tetrahydro-2-isoquinolinyl)propoxy]phenyl]-3-benzoylbenzamide The coupling of 3-benzoylbenzoic acid (0.4 g) with 4-[3-(1,2,3,4-tetrahydro-2-isoquinolinyl)propoxy]benzenamine (Intermediate 88 in EP-A-494623) (0.5 g) gave the title compound (0.37 g) as a solid, mp=180°.

Analysis Found: C, 70.21; H, 5.57; N, 4.88; $C_{32}H_{30}N_2O_3C_2H_2O_4$ Requires: C, 70.33; H, 5.56; N, 4.82%.

EXAMPLE 103

N-[4-(2-(Benzylmethylamino)ethoxy)phenyl]-3-benzoylbenamide

The coupling of 3-benzoylbenzoic acid (0.8 g) with Intermediate 19 (0.9 g) gave the title compound as an oil (1.1 g), hydrochloride (from diethyl ether), mp=140°.

Analysis Found: C, 71.35; H, 5.85; Cl, 6.91; N, 5.43; $C_{30}H_{27}N_2O_3$, HCl Requires: C, 71.92; H, 5.83; Cl, 7.08;

EXAMPLE 104

N-[4-[4-(1,2,3,4-Tetrahydro-6,7-dimethoxy-2-isoquinolinyl)butyl]phenyl]-4-oxo-2-phenyl-4H-1-benzopyran-8-carboxamide A mixture of 4-oxo-2-phenyl-4H-1-benzopyran-8-carboxylic acid* (1 g) and 1-hydroxybenzotriazole (0.58 g) in DMF (50 ml) was stirred at room temperature for 10 min. 4-[4-(1,2,3,4-Tetrahydro-6,7-dimethoxy-2-isoquinolinyl)butyl]benzenamine (intermediate 2(d) in EP-A-494623) (1.1 g) was then added, followed by dicyclohexylcarbodiimide (0.67 g) and the mixture was stirred at room temperature for 16 h and then filtered. The filtrate was concentrated in vacuo, treated with dilute sodium hydroxide solution and extracted with methylene chloride. The combined, dried, organic extracts were evaporated and the residue was purified by column chromatography on silica gel eluting with methylene chloride/methanol (99:1) to give the title compound (0.6 g) as a white solid, after crystallisation from ethyl acetate, mp=117°–120°.

Analysis Found: C, 74.40; H, 6.22; N, 4.63; O, 14.49; $C_{37}H_{36}N_2O_5 0.5H_2O$ Requires: C, 74.35; H, 6.24; N, 4.68; O, 14.72%

*Paolo Da Re E. Sianesi and V. Mancini, Chem. Ber., 1966, 99, 1962.

The following compounds were prepared in a similar manner:

EXAMPLE 105

N-[4-(3-(Methylveratrylamino)propylthiol phenyl]-1,4-dihydro-4-oxo-3-phenyl-8-quinolinecarboxamide The coupling of 1,4-dihydro-4-oxo-2-phenyl-8-quinolinecarboxylic acid* (0.68 g) with N-[3-[(4-aminophenyl)thio]propyl]-3,4-dimethoxy-N-methylbenzenemethanamine (intermediate 38(d) in EP-A-494623) (0.88 g) gave, after crystallisation from isopropanol, the title compound as a solid (0.1 g), mp=130°.

Analysis Found: C, 70.89; H, 6.08; N, 6.98; S, 5.50; $C_{35}H_{35}N_3O_4S_1$ Requires: C, 70.80; H, 5.94; N, 7.08; S, 5.40%.

*Graham J Atwell et al., J. Med. Chem. 1989, 32. 396–401.

EXAMPLE 106

N-[4-(3-(Methylveratrylamino)propyl)phenyl]-1,4-dihydro-4-oxo-2-phenyl-8-quinolinecarboxamide The coupling of 1,4-dihydro-4-oxo-2-phenyl-8-quinolinecarboxylic acid (0.89 g) with 4-amino-N-[(3,4-dimethoxyphenyl)methyl]-N-methylbenzenepropanamine (Intermediate 33(f) in EP-A-494623) (0.9 g) gave, after crystallisation from isopropanol, the title compound as a solid (0.47 g), mp=180°.

Analysis Found: $C_{74.73}$; H, 6.28; N, 7.39; $C_{35}H_{35}N_3O_4$ Requires: C, 74.84; H, 6.28; N, 7.48%.

EXAMPLE 107

N-[4-(2-(Methylveratrylamino)ethoxy)phenyl]-1,4-dihydro-4-oxo-2-phenyl-8-quinolinecarboxamide The coupling of 1,4-dihydro-4-oxo-2-phenyl-8-quinolinecarboxylic acid (0.8 g) with N-[2-(4-aminophenoxy)ethyl]-3,4-dimethoxy-N-methylbenzenemethanamine (Intermediate 36(b) in EP-A-494623) (0.95 g) gave, after crystallisation from ethanol, the title compound as a solid (0.6 g), mp=175°.

Analysis Found: C, 72.50; H, 5.82; N, 7.45; $C_{34}H_{33}N_3O_5$ Requires: C, 72.45; H, 5.90; N, 7.45%.

EXAMPLE 108

N-[4-(4-(Methylveratrylamino)butyl)phenyl]-1,4-dihydro-4-oxo-2-phenyl-8-quinolinecarboxamide The coupling of 1,4-dihydro-4-oxo-2-phenyl-8-quinolinecarboxylic acid (0.8 g) with 4-amino-N-[(3,4-dimethoxyphenyl)methyl]-N-methylbenzenebutanamine (Intermediate 33(a) in EP-A-494623) (0.52 g) gave, after crystallisation from diisopropyl ether, the title compound as a solid (0.13 g), mp=171°.

Analysis Found: C, 72.11; H, 6.59; N, 6.89; $C_{36}H_{37}N_3O_4$, $H_2O$ Requires: C, 72.76; H, 6.57; N, 7.06%.

EXAMPLE 109

N-[4-[2-(1,2,3,4-Tetrahydro-6,7-dimethoxy-2-isoquinolinyl)ethyl]phenyl]-4-oxo-2-phenyl-4H-1-benzopyran-8-carboxamide The coupling of 4-oxo-2-phenyl-4H-1-benzopyran-8-carboxylic acid (0.5 g) with 4-[2-(1,2,3,4-tetrahydro-6,7-dimethoxy-2-isoquinolinyl)ethyl]benzenamine (Intermediate 2(c) in EP-A-494623) (0.58 g) gave, after crystallisation from acetonitrile, the title compound (0.3 g) as a solid, mp 135°–140°.

Analysis Found: C, 73.17; H, 5.78; N, 4.87; O, 16.38; $C_{35}H_{32}N_2O_5 0.75H_2O$ Requires: C, 73.21; H, 5.88; N, 4.85; O, 16.02%.

EXAMPLE 110

N-[4-[4-(1,2,3,4-Tetrahydro-6,7-dimethoxy-2-isoquinolinyl)butyl]phenyl]-2-(3-methoxyphenyl)-4-oxo-4H-1-benzopyran-8-carboxamide The coupling of 2-(3-methoxyphenyl)4-oxo-4H-1-benzopyran-8-carboxylic acid (0.5 g) with 4-[4-(1,2,3,4-tetrahydro-6,7-dimethoxy-2-isoquinolinyl butyl] benzenamine (Intermediate 2(d) in EP-A-494623) (0.52 g) gave, after crystallisation from ethyl acetate, the title compound (0.45 g) as a solid, mp=152°.

Analysis Found: C, 73.22; H, 6.21; N, 4.44; O, 16.09; $C_{38}H_{38}N_2O_6 \cdot 0.25H_2O$ Requires: C, 73.23; H, 6.22; N, 4.49; O, 16.04%.

EXAMPLE 111

N-[4-[4-(1,2,3,4-Tetrahydro-6,7-dimethoxy-2-isoquinolinyl)butyl]phenyl]-1,4-dihydro-4-oxo-2-phenyl-8-quinolinecarboxamide The coupling of 1,4-dihydro-4-oxo-2-phenyl-8-quinolinecarboxylic acid (0.4 g) with 4-[4-(1,2,3,4-tetrahydro-6,7-dimethoxy-2-isoquinolinyl)butyl] benzenamine (Intermediate 2(d) in EP-A-494623) (0.47 g) gave, after crystallisation from isopropanol, the title compound (100 mg) as a solid, mp=204°.

Analysis Found: C, 75.01; H, 6.31; N, 7.01; O, 11.60; $C_{37}H_{37}N_3O_4 \cdot 0.25H_2O$ Requires: C, 75.04; H, 6.38; N, 7.09; O, 11.48%.

EXAMPLE 112

N-[4-[4-(1,2,3,4-Tetrahydro-6,7-dimethoxy-2-isoquinolinyl)butyl]phenyl]-1,4-dihydro-2-(3-methoxyphenyl)-4-oxo-8-quinolinecarboxamide The coupling of 1,4-dihydro-2-(3-methoxyphenyl)-4-oxo-8-quinolinecarboxylic acid (0.22 g) with 4-[4-(1,2,3,4-tetrahydro-6,7-dimethoxy-2-isoquinolinyl)butyl] benzenamine (Intermediate 2(d) in EP-A-494623) (0.25 g) gave, after crystallisation from ethyl acetate, the title compound (50 mg) as a solid, mp=116°.

Analysis Found: C, 71.32; H, 6.45; N, 6.63; $C_{38}H_{39}N_3O_5 \cdot 1.25H_2O$ Requires: C, 71.28; H, 6.53; N, 6.56%.

EXAMPLE 113

In vitro cytotoxicity of MDR inhibitors in Chinese Hamster Ovary cells

The multidrug resistant Chinese Hamster Ovary (CHO) cell line $CH^RC5$ was obtained from Dr V Ling, Princess Margaret Hospital, Toronto, Canada and maintained as anchorage-dependent monolayers in α-minimum essential medium supplemented with thymidine, adenosine, 10% fetal bovine serum, 2 mM L-glutamine (Flow), 100 units/ml penicillin and 100 μg/ml streptomycin in a humidified atmosphere of 95% air and 5% carbon dioxide: Cells were passaged into culture flasks twice a week after dissociation with EDTA.

$CH^RC5$ cells were seeded at a density of $10^4$ cells/well in microtitre plates. After 24 hours, the medium was removed and replaced by 0.1 ml of fresh medium containing successive two-fold dilutions of MDR inhibitors. Each MDR inhibitor was assayed in duplicate in two-fold dilution from 1250 to 20 nM. The last well of each column was utilised to verify the lack of toxicity at the top dose of the MDR inhibitor in the absence of doxorubicin. Other control conditions were assayed on each microtitre plate: cells alone (1 well), doxorubicin alone (7 wells), amiodarone (a range of two-fold dilutions starting at 5 μM; two wells each). 0.1 ml of a 10 μg/ml solution of doxorubicin was added. After 72 hours incubation cell viability was assessed by the reduction of 3-[4,5-dimethylthiazol-2-yl]-2,5-diphenyltetrazolium bromide (MTT; Sigma) to a dark blue formazan product. In particular, 20 μl of a 5 mg/ml solution of MTT prepared in phosphate buffered saline was added to each well. After 4 hours incubation at 37°, the medium was aspirated and replaced with 0.1 ml dimethylsulphoxide. After vigorous shaking, the quantity of formazan product formed was assessed by its optical density at 550 nm. The absorbance is directly related to the number of surviving cells in the wells.

Cytotoxicity calculations were performed on the average of the two wells for each condition. The concentration of each MDR inhibitor giving a 50% reduction of the optical density relative to cells treated with doxorubicin alone was determined to give an $EC_{50}$ value.

Results

In the above test the compounds of the specific Examples hereinabove had $EC_{50}$ values of less than 1 μM and are therefore more potent than prototype MDR inhibitors including amiodarone ($EC_{50}$ 3 μM) and verapamil (3 μM).

The following are examples of pharmaceutical compositions according to the invention. The term 'Active Ingredient' as used hereinafter means a compound of the invention and may be for example a compound of Examples 1–112.

EXAMPLE A

Oral Tablet

|  | Per Tablet (mg) |
| --- | --- |
| Active Ingredient | 50.0 |
| Microcrystalline Cellulose | 110.0 |
| Lactose | 67.5 |
| Sodium Starch Glycolate | 20.0 |
| Magnesium Stearate | 2.5 |
| Total | 250.0 |

The drug is sieved through a 250 μm sieve and then the five powders are intimately mixed in a blender and compressed on ⅜ inch standard concave punches in a tabletting machine.

EXAMPLE B

Oral Capsule

|  | Per Capsule (mg) |
| --- | --- |
| Active Ingredient | 50.0 |
| Microcrystalline Cellulose | 66.5 |
| Lactose USP | 66.5 |
| Sodium Starch Glycolate | 15.0 |
| Magnesium Stearate | 2.0 |
| Total | 200.0 |

The drug is sieved through a 250 μm sieve and then the five powders are intimately mixed in a blender and filled into No. 2 hard gelatin capsule shells on a capsule filling machine.

EXAMPLE C

Injection for Intravenous Administration (10 mg in 10 mL)

|  | % w/w |
|---|---|
| Active Ingredient | 0.1 |
| Cancer chemotherapy agent | as required |
| Water for Injection to | 100.0 |
| Dilute hydrochloric acid to | pH 3.0 |

The active ingredient (and cancer chemotherapy agent where appropriate) is dissolved with mixing in the Water For Injection, adding acid slowly until the pH is 3.0. The solution is sparged with nitrogen and filtratively sterilized through a sterilized filter of 0.22 micron pore size. Under aseptic conditions this sterile solution is placed into sterile ampoules and the ampoules flame sealed.

EXAMPLE D

Oral Syrup

|  | % w/v |
|---|---|
| Active Ingredient | 2.0 |
| Cancer chemotherapy agent | as required |
| Dilute hydrochloric acid to | pH 3.0 |
| Sorbitol solution | 60 v/v |
| Flavour | as required |
| Distilled water to | 100 |

The active ingredient (and cancer chemotherapy agent where appropriate) is dissolved in some of the water with stirring by adding gradually the hydrochloric acid until the pH is 3.0. The sorbitol solution, flavour and the rest of the water are added and the pH re-adjusted to 3.0. The syrup is clarified by filtration through suitable filter pads.

We claim:

1. A compound of formula (Ia)

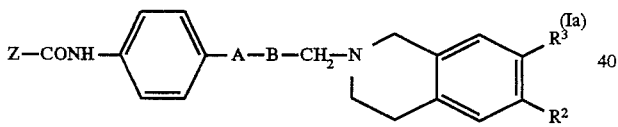

wherein Z represents

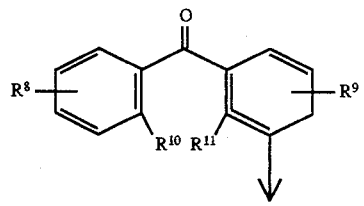

or

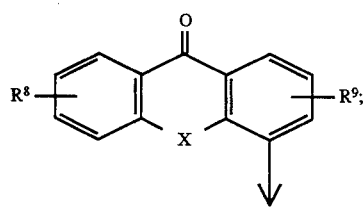

X represents an oxygen atom or NH;

A represents an oxygen or a sulphur atom, a bond or a group $(CH_2)_l NR^7$ where $l$ represents zero or 1 and $R^7$ represents a hydrogen atom or a methyl group;

B represents a $C_{1-4}$ alkylene chain optionally substituted by a hydroxyl group, except that the hydroxyl group and moiety A cannot be attached to the same carbon atom when A represents an oxygen or sulphur atom or a group $(CH_2)_l NR^7$, or when A represents a bond B may also represent a $C_{2-4}$ alkenylene chain;

$R^2$ represents a hydrogen or a halogen atom, or a $C_{1-4}$ alkyl, $C_{1-4}$ alkoxy or $C_{1-4}$ alkylthio group;

$R^3$ represents a hydrogen atom or a $C_{1-4}$ alkoxy group;

$R^8$ represents a hydrogen or halogen atom or a $C_{1-4}$ alkyl, $C_{1-4}$ alkoxy, $C_{1-4}$ alkylthio or nitro group;

$R^9$ represents a hydrogen or halogen atom or a $C_{1-4}$ alkyl, $C_{1-4}$ alkoxy or $C_{1-4}$ alkylthio group;

$R^{10}$ and $R^{11}$ each represent a hydrogen atom or together form a bond or a linking atom selected from —O—, —S— and NH;

and physiologically acceptable salts and solvates thereof.

2. A compound according to claim 1 in which $R^8$ represents a hydrogen or fluorine atom or a $C_{1-4}$ alkoxy or a $C_{1-4}$ alkyl group and $R^9$ represents a hydrogen atom.

3. A pharmaceutical composition according to claim 1 in a form suitable for oral, buccal, parenteral or rectal administration.

4. A pharmaceutical composition according to claim 3 in unit dosage form.

5. A compound according to claim 1 in which $R^2$ and $R^3$ each represent a $C_{1-4}$ alkoxy group and $R^6$ represents a hydrogen atom.

6. A compound of formula (Ia)

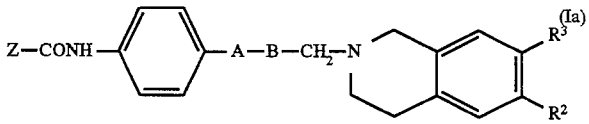

wherein Z is as defined in claim 1 above;

A represents an oxygen or a sulphur atom or a bond;

B represents an unsubstituted $C_{1-4}$ alkylene chain;

$R^2$ and $R^3$ each independently represents a $C_{1-4}$ alkoxy group; and physiologically acceptable salts and solvates thereof.

7. A compound according to claim 6 in which Z represents

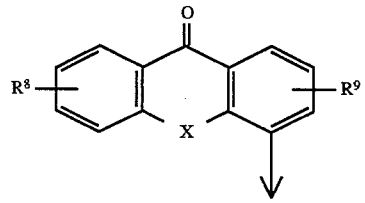

wherein $R^8$ represents a hydrogen or halogen atom or a $C_{1-4}$ alkyl, $C_{1-4}$ alkoxy, $C_{1-4}$ alkylthio or nitro group, $R^9$ represents a hydrogen or halogen atom or a $C_{1-4}$ alkyl, $C_{1-4}$ alkoxy or $C_{1-4}$ alkylthio group and X represents an oxygen atom or NH.

8. A pharmaceutical composition which comprises an effective amount of a compound according to claim 1 together with one or more physiologically acceptable carriers or excipients.

9. A pharmaceutical composition according to claim 8 in a form suitable for oral, buccal, parenteral or rectal administration.

10. A pharmaceutical composition according to claim 8 in unit dosage form.

11. A pharmaceutical composition according to claim 3 in a form suitable for oral administration.

* * * * *